United States Patent
Ito et al.

(10) Patent No.: US 10,703,725 B2
(45) Date of Patent: Jul. 7, 2020

(54) PROCESS FOR PRODUCING NOVEL 4-BENZOAZONINE DERIVATIVES

(71) Applicant: NIPPON ZOKI PHARMACEUTICAL CO., LTD., Osaka-shi, Osaka (JP)

(72) Inventors: Taizo Ito, Kato (JP); Xiaoming Liao, Beijing (CN); Zihua Li, Beijing (CN)

(73) Assignee: NIPPON ZOKI PHARMACEUTICAL CO., LTD., Osaka (JP)

( * ) Notice: Subject to any disclaimer, the term of this patent is extended or adjusted under 35 U.S.C. 154(b) by 27 days.

(21) Appl. No.: 15/755,275

(22) PCT Filed: Aug. 26, 2016

(86) PCT No.: PCT/JP2016/074902
§ 371 (c)(1),
(2) Date: Feb. 26, 2018

(87) PCT Pub. No.: WO2017/038656
PCT Pub. Date: Mar. 9, 2017

(65) Prior Publication Data
US 2018/0258047 A1   Sep. 13, 2018

(30) Foreign Application Priority Data
Aug. 28, 2015 (JP) .................. 2015-169840

(51) Int. Cl.
| C07D 223/04 | (2006.01) |
| A61K 31/55 | (2006.01) |
| A61P 29/00 | (2006.01) |
| C07D 223/14 | (2006.01) |
| C07B 51/00 | (2006.01) |

(52) U.S. Cl.
CPC .......... *C07D 223/04* (2013.01); *C07D 223/14* (2013.01); *A61K 31/55* (2013.01); *C07B 51/00* (2013.01)

(58) Field of Classification Search
CPC ..... C07D 233/04; C07D 223/04; A61K 31/55
See application file for complete search history.

(56) References Cited

FOREIGN PATENT DOCUMENTS

| JP | S55-036403 A | 3/1980 |
| JP | S57-046965 A | 3/1982 |
| JP | S59-130872 A | 7/1984 |
| JP | 2011-503150 A | 1/2011 |
| JP | 2011-511817 A | 4/2011 |
| WO | 2009/063061 A2 | 5/2009 |
| WO | 2009/100872 A1 | 8/2009 |

OTHER PUBLICATIONS

Chen, Qiang, et al. "Asymmetric Syntheses of (-)-Pentazocine and (-)-Eptazocine through an Aza-Prins Cyclization". Chemistry, An Asian Journal, vol. 7, No. 11, pp. 2543-2546, 2012.
Feb. 11, 2019 Extended Search Report issued in European Patent Application No. 16841688.1.
Oct. 25, 2016 International Search Report issued in International Patent Application No. PCT/JP2016/074902.
Prasad et al., "Cyclialkylation Studies. 3. Acid-Catalyzed Cyclodehydration of Some Benzyltertralois, with and without Rearrangement, To Yield Tetracyclic Hydrocarbons", Journal of Organic Chemistry, vol. 56, No. 9, pp. 2998-3000, 1991.
5th Edition Jikken Kagaku Kozxa 13 Yuki Kagobutsu no Gosei I, pp. 211-212, 2004.

*Primary Examiner* — Emily A Bernhardt
*Assistant Examiner* — Laura M Daniel
(74) *Attorney, Agent, or Firm* — Oliff PLC

(57) ABSTRACT

An object of the present invention is to provide a novel tetrahydroazepine compound and a process for producing the same.
The present invention relates to a tetrahydroazepine compound represented by the formula (10) or a salt thereof, and a process for producing the said compound or a salt thereof.

[chem. 1]

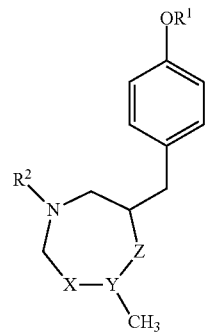

(10)

(In the formula,
$R^1$ is an optionally substituted alkyl group,
$R^2$ is an optionally substituted alkyl group and
one of the X—Y bond and the Y—Z bond is a carbon-carbon double bond and the other is a carbon-carbon single bond).

11 Claims, No Drawings

PROCESS FOR PRODUCING NOVEL 4-BENZOAZONINE DERIVATIVES

TECHNICAL FIELD

The present invention relates to a process for producing novel 4-benzoazonine derivatives.

BACKGROUND ART

Eptazocine hydrobromide is an antagonistic analgesic agent and has been commercially available as an injection preparation where cancerous pain and postoperative pain are the indications.

Patent Document 1 mentions a process for producing a 4-benzoazonine derivative represented by the formula (I) which is an important intermediate for the production of eptazocine hydrobromide in which a perhydroazepine derivative represented by the formula (II) is subjected to a ring closure reaction with Lewis acid.

[chem. 1]

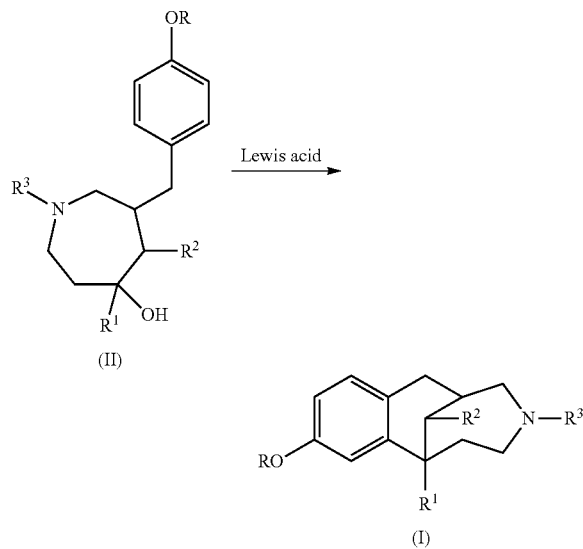

In the Patent Document 1, there are mentioned polyphosphoric acid, hydrobromic acid, etc. as the Lewis acid. However, there is a problem that, since the polyphosphoric acid is a viscous substance, its handling is bad and further that a purifying treatment after producing a ring-closed compound represented by the formula (I) is very difficult.

Accordingly, there has been a demand for a simple, easy and efficient process for producing a 4-benzoazonine derivative where no polyphosphoric acid is used.

In addition, when hydrobromic acid mentioned in the Patent Document 1 is used, the hydrobromic acid which is a volatile strong acid is heated to reflux whereby there is another problem that the reaction condition is severe, that a reaction container is apt to be corroded and that danger is accompanied therewith.

Therefore, it is desirous to avoid the use of hydrobromic acid in view of the health and the safety of persons belonging to the production and the protection of environments.

PRIOR ART DOCUMENTS

Patent Document

Patent Document 1: Gazette of Japanese Patent Laid-Open Publication No. Sho-57/46965 A

SUMMARY OF THE INVENTION

Problems that the Invention is to Solve

An object of the present invention is to provide a novel tetrahydroazepine compound and a process for producing the same. Another object is to provide a process for producing a novel 4-benzoazonine compound.

Means for Solving the Problems

The inventors have eagerly carried out the study for solving the problems in the above Patent Document 1 and, as a result, they have found that the above problems can be solved by adoption of a producing process comprising a step where a compound represented by the formula (10) is produced by the reaction of a compound represented by the formula (9) which will be mentioned later with a specific dehydrating agent and a step where the compound (10) is made to react with an acid. Further investigation has been carried out on the basis of the finding as such whereupon the present invention has now been achieved.

Thus, the present invention provides a tetrahydroazepine compound and a process for producing the same and also provides a process for producing a 4-benzoazonine compound which are as shown below.

Item 1:

A tetrahydroazepine compound represented by the formula (10) or a salt thereof.

[chem. 2]

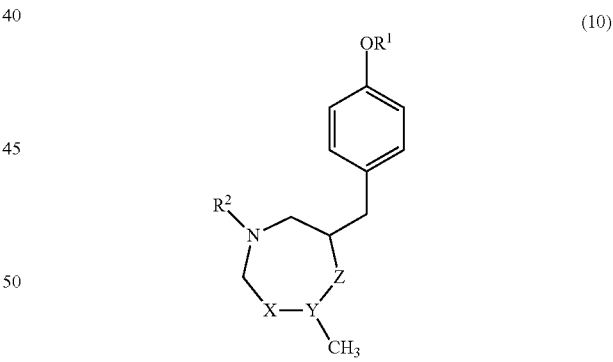

(In the formula,
$R^1$ is an optionally substituted alkyl group,
$R^2$ is an optionally substituted alkyl group and
one of the X—Y bond and the Y—Z bond is a carbon-carbon double bond and the other is a carbon-carbon single bond.)

Item 2:

The compound or the salt thereof according to Item 1, wherein $R^1$ is methyl group and $R^2$ is methyl group in the formula (10).

Item 3:

A process for producing the tetrahydroazepine compound represented by the formula (10) or a salt thereof, comprising (f): a step where a compound represented by the formula (9) or a salt thereof is made to react with at least a dehydrating agent selected from the group consisting of boron trifluoride ether ($BF_3.Et_2O$) complex, trifluoroacetic acid (TFA), trifluoroacetic acid anhydride (TFAA), trimethylsilyl trifluoromethanesulfonate (TMSOTf), aluminum chloride ($AlCl_3$), titanium (IV) chloride ($TiCl_4$), tin (IV) chloride ($SnCl_4$), triphenylmethyl perchlorate ($TrtClO_4$), bismuth triflate ($Bi(OTf)_3$), ytterbium triflate ($Yb(OTf)_3$), scandium triflate ($Sc(OTf)_3$), trifluoromethanesulfonic acid (TfOH), methanesulfonic acid (MsOH), p-toluenesulfonic acid (p-TsOH), benzenesulfonic acid, 10-camphorsulfonic acid (CSA) and phosphorus pentaoxide ($P_2O_5$).

[chem. 3]

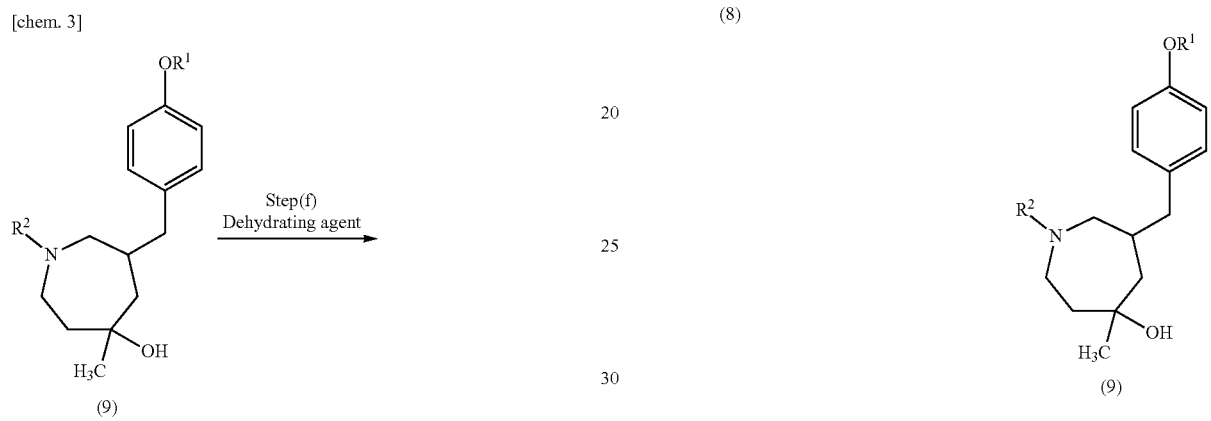

(In the formulae, $R^1$ is an optionally substituted alkyl group, $R^2$ is an optionally substituted alkyl group and one of the X—Y bond and the Y—Z bond is a carbon-carbon double bond and the other is a carbon-carbon single bond.)

Item 4:

The process for producing the tetrahydroazepine compound represented by the formula (10) or a salt thereof according to Item 3, further comprising (e): a step where a compound represented by the formula (8) or a salt thereof is made to react with a methylating agent to give a compound represented by the formula (9) or a salt thereof.

(In the formulae, $R^1$ and $R^2$ have the same meanings as mentioned already.)

Item 5:

The process for producing the tetrahydroazepine compound represented by the formula (10) or a salt thereof according to Item 4, further comprising (d): a step where a compound represented by the formula (7) or a salt thereof is made to react with an acid to give a compound represented by the formula (8) or a salt thereof.

[chem. 5]

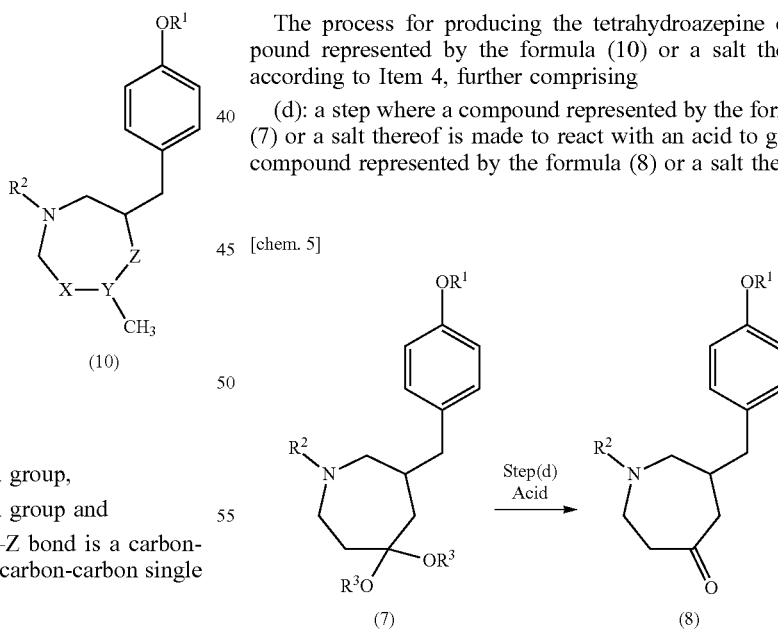

(In the formulae, $R^1$ and $R^2$ have the same meanings as mentioned already and the two $R^3$'s are the same or different, and each is an optionally substituted alkyl group or the two $R^3$'s may be bonded each other to form a ring together with oxygen atoms to which the two $R^3$'s are bonded.)

Item 6:

The process for producing the tetrahydroazepine compound represented by the formula (10) or a salt thereof according to Item 5, further comprising (c): a step where a compound represented by the formula (6) or a salt thereof is made to react with a reducing agent to give a compound represented by the formula (7) or a salt thereof.

[chem. 6]

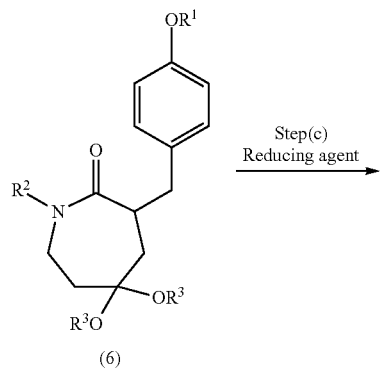

(In the formulae, $R^1$, $R^2$, $R^2$ and $R^3$ have the same meanings as mentioned already.)

Item 7:

The process for producing the tetrahydroazepine compound represented by the formula (10) or a salt thereof according to Item 6, further comprising (b): a step where a compound represented by the formula (5) or a salt thereof is made to react with a compound represented by the formula (15) to give a compound represented by the formula (6) or a salt thereof.

[chem. 7]

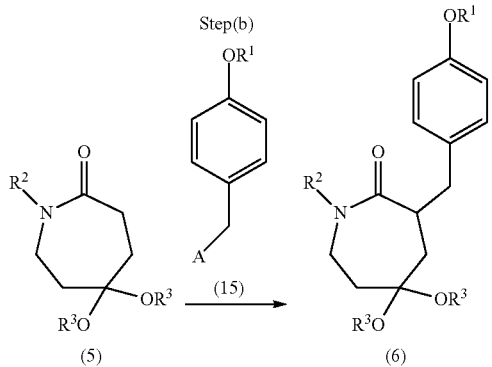

(In the formulae, $R^1$, $R^2$, $R^2$ and $R^3$ have the same meanings as mentioned already and A is an eliminating group.)

Item 8:

The process for producing the tetrahydroazepine compound represented by the formula (10) or a salt thereof according to Item 7, further comprising (a): a step where a compound represented by the formula (4) or a salt thereof is made to react with an alkylating agent to give a compound represented by the formula (5) or a salt thereof.

[chem. 8]

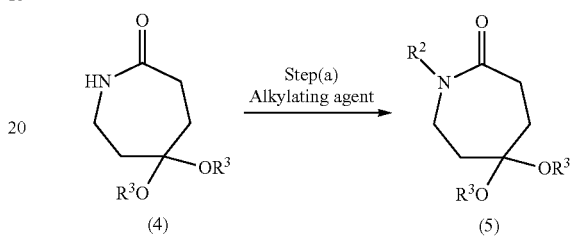

(In the formulae, $R^2$ and $R^3$ have the same meanings as mentioned already.)

Item 9:

A process for producing the 4-benzoazonine compound presented by the formula (11) or a salt thereof, comprising (g): a step where a tetrahydroazepine compound represented by the formula (10) or a salt thereof is made to react with an acid.

[chem. 9]

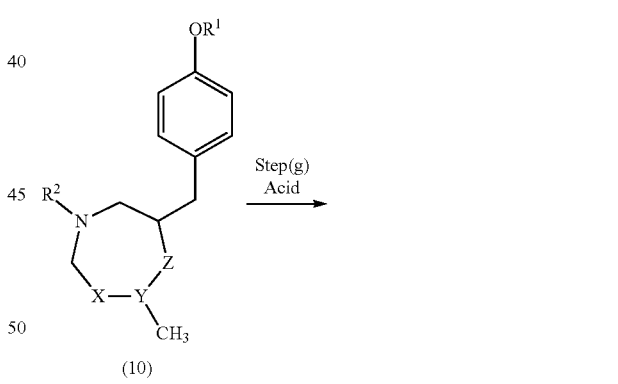

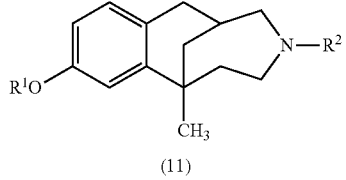

(In the formulae, $R^1$ is an optionally substituted alkyl group, $R^2$ is an optionally substituted alkyl group and one of the X—Y bond and the Y—Z bond is a carbon-carbon double bond and the other is a carbon-carbon single bond.)

Item 10:

The process for producing the 4-benzoazonine compound represented by the formula (11) or a salt thereof according to Item 9, comprising the step(s) mentioned in any of Items 3 to 8.

Item 11:

A process for producing a compound represented by the formula (13) or a salt thereof, comprising the step(s) mentioned in any of Items 3 to 10 and further comprising (h): a step where a 4-benzoazonine compound represented by the formula (11) or a salt thereof is made to react with an organic acid to give a compound represented by the formula (12) or salt thereof and (i) a step where an $OR^1$ group in the compound represented by the formula (12) or a salt thereof is deprotected to give the compound represented by the formula (13) or a salt thereof.

[chem. 10]

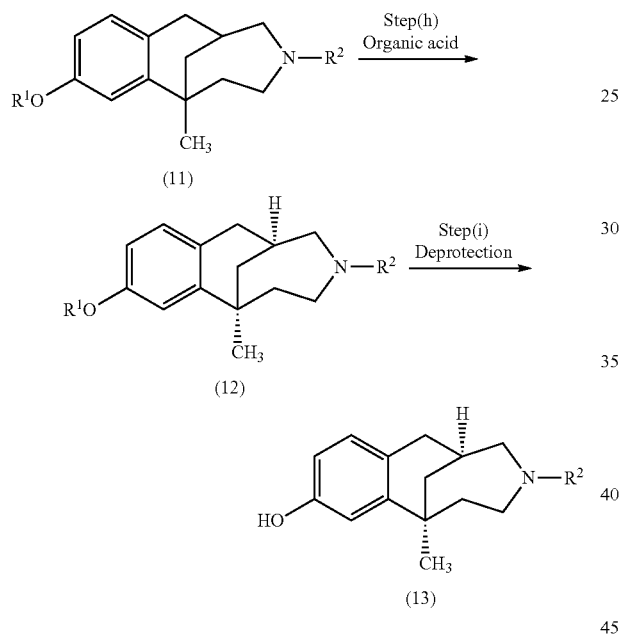

(In the formulae, $R^1$ and $R^2$ have the same meanings as mentioned already.)

Effect of the Invention

The present invention is a novel process for producing a tetrahydroazepine compound and a 4-benzoazonine compound and is a producing process which is desirous in view of the health and safety of persons working for the production and also of the protection of environments. In addition, it is now possible to isolate and purity the aimed product without troublesome purification step throughout the whole production steps whereby the present invention is suitable as an efficient production process in an industrial scale.

MODE FOR CARRYING OUT THE INVENTION

Hereinafter, the present invention will be specifically illustrated.

1. Producing Process for a Compound Represented by the Formula (13)

The compound represented by the formula (13) is produced by the reaction steps shown in the reaction formula 1.

Reaction formula 1

[chem. 11]

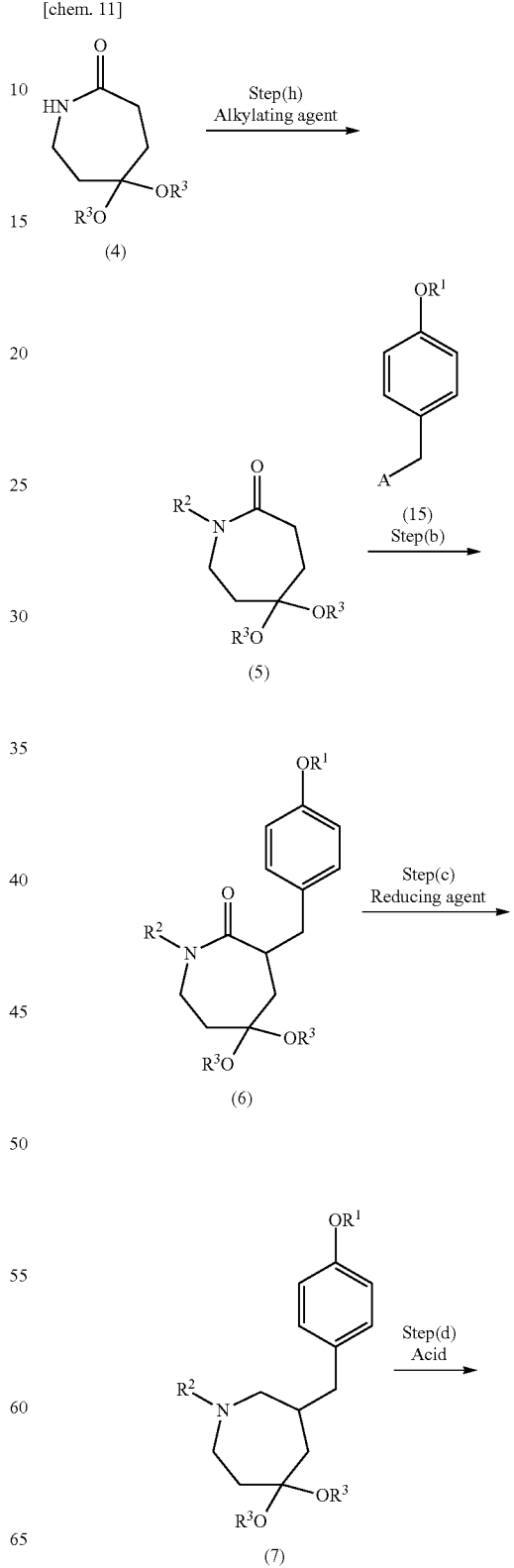

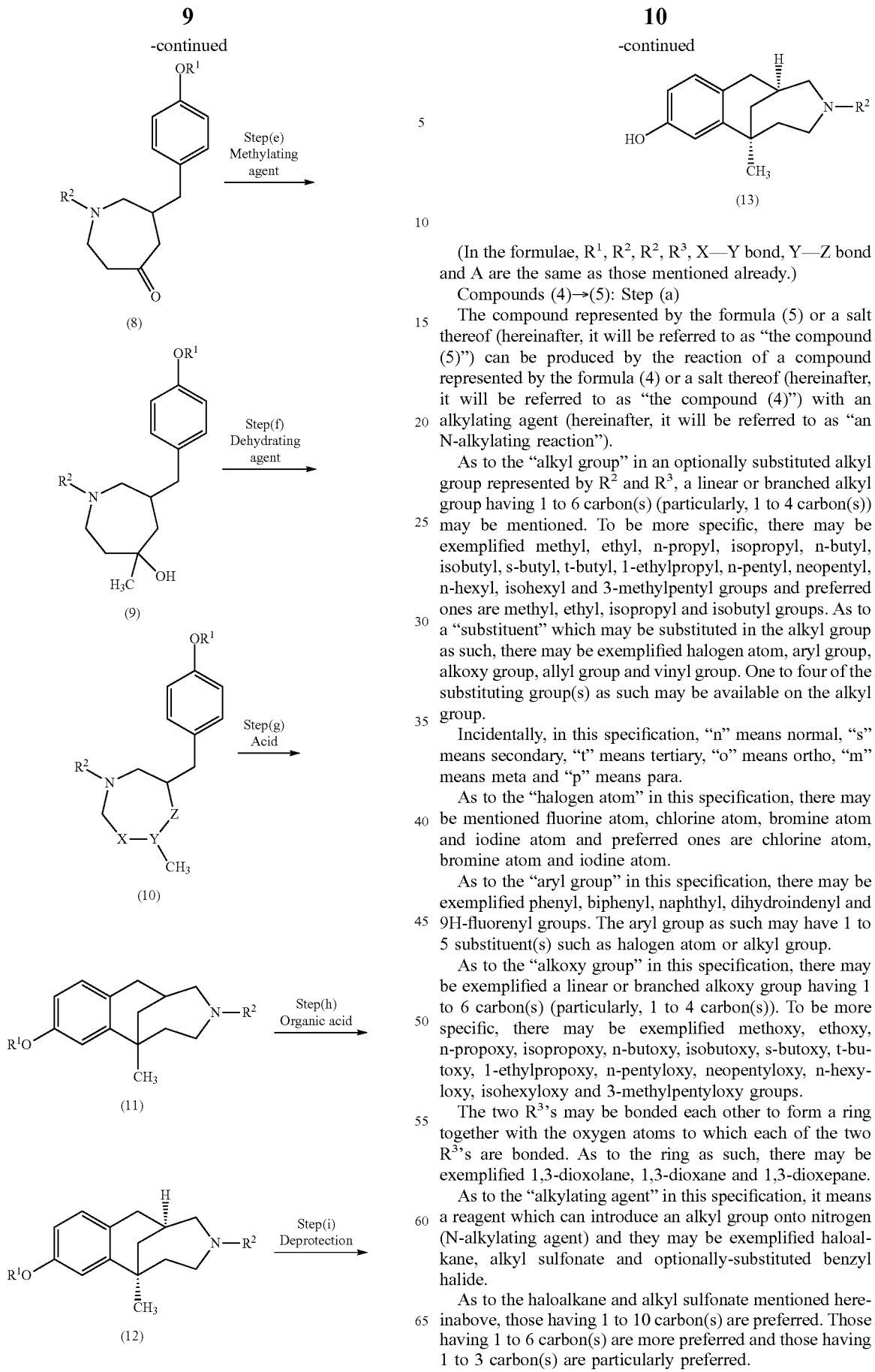

(In the formulae, $R^1$, $R^2$, $R^2$, $R^3$, X—Y bond, Y—Z bond and A are the same as those mentioned already.)

Compounds (4)→(5): Step (a)

The compound represented by the formula (5) or a salt thereof (hereinafter, it will be referred to as "the compound (5)") can be produced by the reaction of a compound represented by the formula (4) or a salt thereof (hereinafter, it will be referred to as "the compound (4)") with an alkylating agent (hereinafter, it will be referred to as "an N-alkylating reaction").

As to the "alkyl group" in an optionally substituted alkyl group represented by $R^2$ and $R^3$, a linear or branched alkyl group having 1 to 6 carbon(s) (particularly, 1 to 4 carbon(s)) may be mentioned. To be more specific, there may be exemplified methyl, ethyl, n-propyl, isopropyl, n-butyl, isobutyl, s-butyl, t-butyl, 1-ethylpropyl, n-pentyl, neopentyl, n-hexyl, isohexyl and 3-methylpentyl groups and preferred ones are methyl, ethyl, isopropyl and isobutyl groups. As to a "substituent" which may be substituted in the alkyl group as such, there may be exemplified halogen atom, aryl group, alkoxy group, allyl group and vinyl group. One to four of the substituting group(s) as such may be available on the alkyl group.

Incidentally, in this specification, "n" means normal, "s" means secondary, "t" means tertiary, "o" means ortho, "m" means meta and "p" means para.

As to the "halogen atom" in this specification, there may be mentioned fluorine atom, chlorine atom, bromine atom and iodine atom and preferred ones are chlorine atom, bromine atom and iodine atom.

As to the "aryl group" in this specification, there may be exemplified phenyl, biphenyl, naphthyl, dihydroindenyl and 9H-fluorenyl groups. The aryl group as such may have 1 to 5 substituent(s) such as halogen atom or alkyl group.

As to the "alkoxy group" in this specification, there may be exemplified a linear or branched alkoxy group having 1 to 6 carbon(s) (particularly, 1 to 4 carbon(s)). To be more specific, there may be exemplified methoxy, ethoxy, n-propoxy, isopropoxy, n-butoxy, isobutoxy, s-butoxy, t-butoxy, 1-ethylpropoxy, n-pentyloxy, neopentyloxy, n-hexyloxy, isohexyloxy and 3-methylpentyloxy groups.

The two $R^3$'s may be bonded each other to form a ring together with the oxygen atoms to which each of the two $R^3$'s are bonded. As to the ring as such, there may be exemplified 1,3-dioxolane, 1,3-dioxane and 1,3-dioxepane.

As to the "alkylating agent" in this specification, it means a reagent which can introduce an alkyl group onto nitrogen (N-alkylating agent) and they may be exemplified haloalkane, alkyl sulfonate and optionally-substituted benzyl halide.

As to the haloalkane and alkyl sulfonate mentioned hereinabove, those having 1 to 10 carbon(s) are preferred. Those having 1 to 6 carbon(s) are more preferred and those having 1 to 3 carbon(s) are particularly preferred.

As to the haloalkane, there may be exemplified methyl chloride, ethyl chloride, methyl bromide, ethyl bromide, methyl iodide and ethyl iodide.

As to the alkyl sulfonate, there may be exemplified methyl methanesulfonate, ethyl methanesulfuonate, methyl ethanesulfonate, ethyl ethanesulfonate, methyl p-toluenesulfonate and ethyl p-toluenesulfonate.

As to the benzyl halide, there may be exemplified benzyl chloride and benzyl bromide and, as to the substituent therefor, there may be exemplified alkyl group, alkoxy group and halogen atom.

Preferred alkylating agent are methyl p-toluenesulfonate, methyl methanesulfonate, methyl iodide, methyl bromide and methyl chloride and more preferred one is methyl iodide.

Usually, the reaction of the above step (a) may be carried out in a solvent in the presence of a base. As to the solvent, anything may be acceptable provided that it does not badly affect the reaction and examples thereof are an aromatic hydrocarbon solvent (such as toluene and xylene); a ketone solvent (such as acetone and methyl ethyl ketone); an ether solvent (such as tetrahydrofuran (THF), methyl t-butyl ether (MTBE), dioxane, diethyl ether, dimethoxyethane and diglyme); an alcohol solvent (such as t-butanol); an ester solvent (such as methyl acetate and ethyl acetate); an aprotic polar solvent (such as acetonitrile, N,N-dimethylformamide (DMF) and dimethyl sulfoxide (DMSO)); a halogenated hydrocarbon solvent (such as methylene chloride (DCM) and 1,2-dichloroethane (DCE)); and a mixed solvent thereof. Preferred ones are toluene and THF and more preferred one is toluene.

As to the base, known inorganic base and organic base may be used. As to the inorganic base, there is no particular limitation provided that it is a compound which can be easily handled and examples thereof are alkali metal hydrogen carbonate (such as lithium hydrogen carbonate, sodium hydrogen carbonate and potassium hydrogen carbonate); alkali metal hydroxide (such as lithium hydroxide, sodium hydroxide, potassium hydroxide and cesium hydroxide); alkali metal carbonate (such as lithium carbonate, sodium carbonate, potassium carbonate and cesium carbonate); and alkali metal alkoxide (having 1 to 4 carbon(s)) such as sodium methoxide, sodium ethoxide and potassium t-butoxide).

As to the organic base, there may be exemplified trialkylamine (such as trimethylamine, triethylamine and N,N-diisopropylethylamine), pyridine, quinoline, piperidine, imidazole, picoline, 4-dimethylaminopyridine, N,N-dimethylaniline, N-methylmorpholine, 1,5-diazabicyclo[4.3.0]non-5-ene (DBN), 1,4-diazabicyclo[2.2.2]octane (DABCO) and 1,8-diazabicyclo[5.4.0]undec-7-ene (DBU). When the base as such is liquid, it may be used as a solvent as well.

Preferred bases are alkali metal carbonate (particularly, sodium carbonate, potassium carbonate and cesium carbonate) and alkali metal (having 1 to 4 carbon(s)) alkoxide (such as potassium t-butoxide) and more preferred one is potassium t-butoxide. Each of those bases may be used solely or two or more thereof may be used jointly.

The amount of the base used for 1 mol of the compound (4) is usually 1 to 10 mol or, preferably, 1 to 5 mol.

If necessary, the above reaction may be carried out by adding alkali metal iodide such as potassium iodide or sodium iodide as a reaction promoter to the reaction system.

When the reaction promoter is used, its amount used for 1 mol of the compound (4) is usually 0.1 to 10 mol and, preferably, about 1 to 5 mol.

The ratio of the compound (4) to the alkylating agent used for 1 mol of the former is usually at least 1 mol of the latter and, preferably, about 1 to 5 mol of the latter.

There is no particular limitation for the reaction temperature and, usually, the reaction is carried out under any of cooling, room temperature and heating. Preferably, the reaction is to be carried out for 1 to 30 hour(s) under the temperature condition of from about room temperature to about 85° C.

Compounds (5)→(6); Step (b)

The compound represented by the formula (6) or a salt thereof (hereinafter, it will be referred to as "the compound (6)") can be produced by the reaction (hereinafter, it will be referred to as "an alkoxybenzylating reaction) of a compound represented by the formula (5) with a compound represented by the formula (15) (hereinafter, it will be referred to as "the compound (15)").

Usually, the reaction of the step (b) may be carried out in a solvent in the presence of a base.

As to the solvent, anything may be used provided that it does not badly affect the reaction and examples thereof are an aromatic hydrocarbon solvent (such as toluene and xylene); an aliphatic hydrocarbon solvent (such as n-hexane); and an ether solvent (such as THF, MTBE, dioxane, diethyl ether, dimethoxyethane and diglyme). Preferred ones are toluene and THF and more preferred one is toluene.

As to the base, there may be exemplified alkali metal amide such as lithium bis(trimethylsilyl) amide (LHMDS), lithium diisopropyl amide (LDA), sodium bis(trimethylsilyl) amide (SHMDS) and potassium bis(trimethylsilyl) amide (LHMDS); and alkali metal alkoxide such as sodium t-butoxide and potassium t-butoxide. Preferred bases are LDA and LHMDS and more preferred base is LDA. One of those bases may be used solely or two or more thereof may be used jointly.

The amount of the base used for 1 mol of the compound (5) is usually at least 1 mol and, preferably, it is about 1 to 5 mol.

With regard to "alkyl group" and "substituent group" in the optionally-substituted alkyl group represented by $R^1$, they have the same meanings as "alkyl group" and "substituent group" mentioned in the above step (a). Among the $R^1$, preferred ones are methyl group, isopropyl group, cyclohexyl group and benzyl group and more preferred one is methyl group.

A is an eliminating group and examples of the eliminating group are halogen atom (such as chlorine atom, bromine atom and iodine atom), optionally-substituted alkylsufonyloxy group (such as methanesulfonyloxy group, ethanesulfonyloxy group and trifluoromethanesulfonyloxy group) and optionally-substituted arylsulfonyloxy group (such as benzenesulfonyloxy group and p-toluenesulfonyloxy group).

To be more specific, examples of the compound (15) are 4-methoxybenzyl chloride, 4-methoxybenzyl bromide, 4-benzyloxybenzyl chloride and 4-benzyloxybenzyl bromide.

Amount of the compound (15) used for 1 mol of the compound (5) is usually at least 1 mol and, preferably, it is about 1 to 5 mol.

There is no particular limitation for the reaction temperature and, usually, the reaction is carried out under any of cooling, from −80° C. to room temperature and heating. Preferably, the reaction is to be carried out for 1 to 30 hours under the temperature condition of from about −80° C. to room temperature.

Compounds (6)→(7): Step (c)

The process for producing a compound represented by the formula (7) or a salt thereof (hereinafter, it will be referred to as "the compound (7)") includes a step where the compound (6) is made to react with a reducing agent (reduction reaction).

Usually, the reaction of the step (c) may be carried out in a solvent.

As to the solvent, anything may be used provided that it does not badly affect the reaction and examples thereof are an aromatic hydrocarbon solvent (such as toluene and xylene), an ether solvent (such as THF, MTBE, dioxane, diethyl ether, dimethoxyethane and diglyme) and a mixed solvent thereof. Preferred ones are toluene and THF and more preferred one is toluene.

As to a reducing agent, there may be mentioned aluminum hydride which is called a hydride reducing agent such as (i-Bu)$_2$AlH, LiAlH$_4$ [the so-called LAH] and NaAlH$_2$(OC$_2$H$_4$OCH$_3$)$_2$ [sodium bis (2-methoxyethoxy) aluminum hydride or the so-called Red-Al (registered trade mark)]; and boron hydride such as diborane, BH$_3$.THF, BH$_3$.S(CH$_3$)$_2$, BH$_3$.N(CH$_3$)$_2$, NaBH$_4$ and LiBH$_4$ (i-Bu means isobutyl group). Each of those reducing agents may be used solely or two or more may be used jointly.

A preferred reducing agent is Red-Al in such a view that the safety is high, the after-treatment is simple and convenient and the yield of the aimed compound (7) is enhanced.

Amount of the reducing agent used for 1 mol of the compound (6) is usually at least 1 mol and, preferably, about 1 to 5 mol.

There is no particular limitation for the reaction temperature in the reducing reaction and the reaction usually proceeds under any of cooling, room temperature and heating. It is preferred to conduct the reaction for 1 to 30 hour(s) under the temperature condition of from 0° C. to about room temperature.

There is no particular limitation for the method of after-treatment and a crude product of the aimed compound (7) can be prepared when, for example, the usual after-treatment operation is carried out after finishing the reaction. The crude product is subjected to a purifying operation such as the treatment with active charcoal, distillation, recrystallization or column chromatography depending upon the necessity whereupon it can be prepared in high chemical purity.

For example, in such a case where a reaction mixture containing the compound (7) is mixed with water or basic aqueous solution in the purifying step, it is also possible that a chelating agent is further mixed therewith. As to the chelating agent, there are exemplified sodium gluconate, sodium tartrate, sodium potassium tartrate tetrahydrate (Rochelle salt), ethylenediamine tetraacetic acid, diethylenetriamine pentaacetic acid and nitrilotriacetic acid. Preferable one is Rochelle salt. As a result of mixing with a chelating agent as such, a liquid separating property becomes much better.

It is also possible that the compound (7) in the separated organic layer is purified with salt. The purification with salt is a step where the compound (7) is made to act with an acid and induced to a salt whereby it is crystallized.

As to the acid, there are exemplified a carboxylic acid such as tartaric acid (L-tartaric acid, D-tartaric acid), acrylic acid, crotonic acid, citraconic acid, maleic acid, fumaric acid and cis- or trans-cinnamic acid; an aromatic carboxylic acid such as benzoic acid, o-, m- or p-toluic acid, o-, m- or p-fluorobenzoic acid, o-, m- or p-chlorobenzoic acid, o-, m- or p-bromobenzoic acid, o-, m- or p-iodobenzoic acid, o-, m- or p-hydroxybenzoic acid, o-, m- or p-anisic acid, o-, m- or p-aminobenzoic acid, o-, m- or p-nitrobenzoic acid, o-, m- or p-cyanobenzoic acid, o-, m- or p-benzenedicarboxylic acid (phthalic acid, isophthalic acid or terephthalic acid), α-, β- or γ-picolinic acid, 2,6-pyridinedicarboxylic acid, 1- or 2-naphthoic acid, mandelic acid (D-mandelic acid, L-mandelic acid), di-p-toluoyltartaric acid and dibenzoyltartaric acid; and an organic acid such as formic acid, oxalic acid, malonic acid, succinic acid, adipic acid, pimelic acid, cyanoacetic acid, citric acid, glycolic acid, glyoxylic acid, pyruvic acid, levulinic acid, oxalacetic acid, mercaptoacetic acid, phenoxyacetic acid and picric acid.

Among the above, preferred acids are tartaric acid (D-tartaric acid, L-tartaric acid) and o-, m- or p-nitrobenzoic acid and more preferred one is p-nitrobenzoic acid.

There is no particular limitation for the amount of the acid used and, for example, 1 mol or more of the acid may be used for 1 mol of the compound (7). Usually, it is preferred to be 1 to 10 mol and, particularly, 1 to 5 mol is more preferred.

A method for preparing a salt may be appropriately decided by taking the combination of the compound (7) with the acid into consideration. Usually, there is no particular limitation for the temperature in the preparation of a salt and, usually, the reaction proceeds under any of cooling, room temperature and heating. Preferably, the reaction is to be carried out for 1 to 30 hour(s) under the temperature condition of from ice cooling to at about room temperature.

Compounds (7)→(8): Step (d)

The compound represented by the formula (8) or a salt thereof (hereinafter, it will be referred to as "the compound (8)") can be produced by the reaction of the compound (7) with an acid (deacetalizing reaction).

The reaction of the step (d) may be usually carried out without a solvent or in a solvent.

When a solvent is used, any solvent will do provided that it does not badly affect the reaction and examples thereof are water; an aromatic hydrocarbon solvent (such as toluene and xylene); an ether solvent (such as THF, MTBE, dioxane, diethyl ether, dimethoxyethane and diglyme); and a mixed solvent thereof. Preferred ones are water and THF and more preferred one is water.

As to an acid, inorganic and organic acids are mentioned and examples thereof are hydrochloric acid, phosphoric acid, sulfuric acid, acetic acid, TFA and p-TsoH. Among them, the preferred one is hydrochloric acid. When the acid is liquid (aqueous solution), it also plays a role of a solvent. Each of those acids may be used solely or two or more may be used jointly.

Amount of the acid used for 1 mol of the compound (7) is usually at least 1 mol or, preferably, about 5 to 20 mol.

There is no particular limitation for the reaction temperature and, usually, the reaction is carried out under any of cooling, room temperature and heating. Preferably, the reaction may be carried out for 1 to 30 hour(s) under the temperature condition of from about room temperature to about 85° C.

After finishing the reaction of the step (d), neutralization is carried out using an aqueous solution of alkali such as sodium hydroxide followed by extracting with an organic solvent whereupon the aimed compound (8) can be prepared.

Compounds (8)→(9): Step (e)

A compound represented by the formula (9) or a salt thereof (hereinafter, it will be referred to as "the compound (9)") can be produced by the reaction of the compound (8) with a methylating agent (methylation reaction).

Usually, the reaction of the step (e) can be carried out in the presence of a solvent.

As to the solvent, anything may be used provided that it does not badly affect the reaction and examples thereof are an aromatic hydrocarbon solvent (such as toluene and xylene); an ether solvent (such as THF, MTBE, dioxane, diethyl ether, dimethoxyethane and diglyme); and a mixed solvent thereof. Preferred ones are toluene and THF and more preferred one is toluene.

As to a methylating agent, there are exemplified an organic lithium reagent and Grignard reagent.

As to an organic lithium reagent, there is exemplified methyl lithium ($CH_3Li$). As to Grignard reagent, there are exemplified methyl magnesium chloride ($CH_3MgCl$), methyl magnesium bromide ($CH_3MgBr$) and methyl magnesium iodide ($CH_3MgI$). Usually, such a methylating agent is used by diluting with an organic solvent. Among them, the preferred ones are $CH_3MgCl$ and $CH_3Li$ and more preferred one is $CH_3MgCl$. Each of those methylating agents may be used solely or two more thereof may be used jointly.

Usually, the amount of the methylating agent used for 1 mol of the compound (8) is at least 1 mol and, preferably, about 1 to 5 mol.

There is no particular limitation for the reaction temperature and, usually, the reaction is carried out under any of cooling, room temperature and heating. Preferably, the reaction may be carried out for 1 to 30 hour(s) under the temperature condition of from −80° C. to about room temperature.

Compounds (9)→(10): Step (f)

A tetrahydroazepine compound represented by the formula (10) or a salt thereof (hereinafter, it will be referred to as "the compound (10)") can be produced by the reaction of the compound (9) with at least one kind of dehydrating agent selected from the group consisting of $BF_3.Et_2O$ complex, TFA, TFAA, TMSOTf, $AlCl_3$, $TiCl_4$, $SnCl_4$, $TrtClO_4$, $Bi(OTf)_3$, $Yb(OTf)_3$, $Sc(OTf)_3$, TfOH, MsOH, p-TsOH, benzenesulfonic acid, CSA and $P_2O_5$ (dehydrating reaction).

As to the compound (10), there are exemplified a sole tetrahydroazepine compound represented by the following formula (10a) or a salt thereof (hereinafter, it will be referred to as "the compound (10a))", a sole tetrahydroazepine compound represented by the following formula (10b) or a salt thereof (hereinafter, it will be referred to as "the compound (10b))" and a mixture of the compound (10a) with the compound (10b).

[chem. 12]

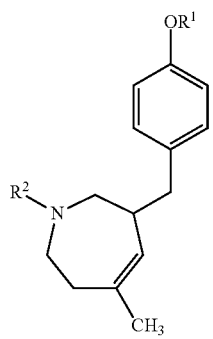

(10a)

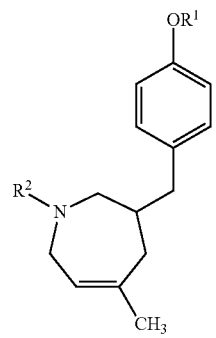

(10b)

The preferred compound (10) is a compound where $R^1$ is methyl group and $R^2$ is methyl group.

The compound (10) of the present invention covers stereoisomer, optical isomer and solvate (such as hydrate and ethanolate).

A salt of the compound (10) of the present invention is a pharmaceutically acceptable salt and examples thereof are a salt with inorganic acid (such as hydrochloride, hydrobromide, hydriodide, sulfate, nitrate and phosphate); and a salt with organic acid (such as formate, acetate, propionate, oxalate, malonate, succinate, fumarate, maleate, lactate, malate, citrate, tartrate, carbonate, picrate, methanesulfonate, ethanesulfonate, p-TsOH salt, glutamate and pamoate).

Hereinafter, the compound (10) and a salt thereof may be sometimes referred to as the compound of the present invention.

As to a dehydrating agent in the step (f), one member may be used solely or two or more thereof may be used jointly.

As to the dehydrating agent, preferred ones are $BF_3.Et_2O$, TFA, TFAA, TfOH, MsOH, p-TsOH, benzenesulfonic acid, CSA and $P_2O_3$ and more preferred ones are $BF_3.Et_2O$ complex, TFA, TFAA, TfoH, p-TsOH and $P_2O_3$.

Amount of the dehydrating agent used for 1 mol of the compound (9) is usually 1 to 10 mol and, preferably, 1 to 6 mol.

Usually, the reaction of the above step (f) may be carried out in the presence of a solvent.

As to a solvent, anything may be used provided that it does not badly affect the reaction and examples thereof are an aromatic hydrocarbon solvent (such as toluene and xylene); an ether solvent (such as THF, MTBE, dioxane, diethyl ether, dimethoxyethane and diglyme); an aprotic polar solvent (such as acetonitrile, DMF and DMSO); a halogenated hydrocarbon solvent (such as DCM and DCE); and a mixed solvent thereof. Preferred ones are toluene and DCE and more preferred one is toluene.

There is no particular limitation for the reaction temperature and, usually, the reaction is carried out under any of cooling, room temperature and heating. Preferably, the reaction may be carried out for 1 to 30 hour(s) under the temperature condition of from about 0° C. to about 120° C.

Compounds (10)→(11): Step (g)

A 4-benzoazonine compound represented by the formula (11) or a salt thereof (hereinafter, it will be referred to as "the compound (11)") can be produced by the reaction of the compound (10) with an acid (cyclization reaction).

Usually, the reaction of the step (g) can be carried out in a solvent.

As to the solvent, anything may be used provided that it does not badly affect the reaction and examples thereof are a halogenated hydrocarbon solvent (such as DCM and DCE); an ether solvent (such as THF, MTBE, dioxane, diethyl ether, dimethoxyethane and diglyme); an alcohol solvent (such as methanol, ethanol, isopropanol, n-butanol, trifluoroethanol and ethylene glycol); and a mixed solvent thereof. An acid which is a reagent (such as MsOH) may also be used as a solvent. Among those, preferred one is a halogenated hydrocarbon solvent and more preferred one is DCM. As to the solvent, an anhydrous solvent is preferred.

As to an acid, there are exemplified inorganic acid, organic acid and Lewis acid. As to the inorganic acid, there are exemplified hydrochloric acid, hydrobromic acid, sulfuric acid, hydrogen chloride and hydrogen bromide. As to the organic acid, there are exemplified a fatty acid such as formic acid, acetic acid and propionic acid; a trihaloacetic acid such as trichloroacetic acid and TFA acid; and a sulfonic acid such as MsOH, ethanesulfonic acid and TfOH. As to the Lewis acid, there are exemplified $BF_3.Et_2O$ complex, boron tribromide, $AlCl_3$ and ferric chloride. One of those acids may be used solely or two or more thereof may be used jointly.

Amount of the acid used for 1 mol of the compound (10) is usually 0.5 to 10 ml or, preferably, 1 to 6 mol.

There is no particular limitation for the reaction temperature and, usually, the reaction can be carried out under any of cooling, room temperature and heating. Preferably, the reaction is carried out for 1 to 30 hour(s) under the temperature condition of about 0° C. to 100° C.

The step (f) and the step (g) may be carried out by means of a one-pot synthesis.

In the step (f) and the step (g), no viscous reaction reagent is used but a reagent having excellent handling ability is used and, moreover, the purifying treatment after producing the compound (11) is simple and convenient whereby a reduction in the manufacturing cost can be expected thereby.

Moreover, in the step (f) and the step (g), no hydrobromic acid which is apt to corrode a reaction container being accompanied with danger is used whereby the steps are excellent in view of the health and safety of the persons in charge of the manufacture and of the protection of environments.

Compounds (11)→(12): Step (h)

The compound represented by the formula (12) or a salt thereof (hereinafter, it will be referred to as "the compound (12)") can be produced by the reaction of the compound (11) with an organic acid (a salt forming reaction)/.

Usually, the reaction of the step (h) can be carried out in a solvent.

As to the solvent, anything may be used provided that it does not badly affect the reaction and examples thereof are a ketone solvent (such as acetone and methyl ethyl ketone); an ether solvent (such as THF, MTBE, dioxane, diethyl ether, dimethoxyethane, diglyme and MTBE); an ester solvent (such as methyl acetate and ethyl acetate); an aprotic polar solvent (such as acetonitrile, DMF and DMSO); a halogenated hydrocarbon solvent (such as DCM and DCE); and a mixed solvent thereof. Preferred ones are ether solvent (particularly, MTBE, etc.) and ester solvent (particularly, ethyl acetate, etc.).

As to an organic solvent, there are exemplified an optically active organic acid such as mandelic acid (D-mandelic acid and L-mandelic acid) and tartaric acid by referring to the gazette of Japanese Examined Patent Publication No. Sho-63/20817 A. Among them, a preferred organic acid is mandelic acid.

Amount of the organic acid used for 1 mol of the compound (11) is usually 0.4 to 10 mol and, preferably, 0.4 to 5 mol.

There is no particular limitation for the reaction temperature and, usually, the reaction can be carried out under any of cooling, room temperature and heating. Preferably, the reaction is carried out for 1 to 30 hour(s) under the temperature condition of about 0 to 60° C.

Since the resulting organic acid is deposited as a solid, it can be collected by filtration. Upon the collection by filtration, the solid can be washed with the above solvent used in the step (h).

After that, the resulting organic acid salt is neutralized using a base (neutralizing step) whereupon the compound (12) can be obtained. As to the base as such, known inorganic base or organic base may be mentioned. As to the inorganic base, there are exemplified aqueous ammonia; hydroxide of alkali metal or of the metal of group II of the periodic table; and carbonate of alkali metal or of the metal of group II of the periodic table. As to the inorganic base, amine or the like may be mentioned.

As to the alkali metal hydroxide, there are exemplified sodium hydroxide, potassium hydroxide, lithium hydroxide and cesium hydroxide. As to the hydroxide of the metal of group II of the periodic table, there are exemplified magnesium hydroxide and calcium hydroxide. As to the carbonate of the alkali metal, there are exemplified sodium carbonate, lithium carbonate and cesium carbonate. As to the carbonate of the metal of group II of the periodic table, there are exemplified magnesium carbonate and calcium carbonate. Preferred base is hydroxide of alkali metal and more preferred one is sodium hydroxide.

Amount of the base used for 1 mol of the acid salt is usually 1 to 5 mol and, preferably, 1 to 2 mol.]

Reaction temperature for the neutralization is usually −10° C. to 50° C. and, preferably, 0° C. to 30° C.

Compounds (12)→(13); Step (i)

The compound represented by the formula (13) or a salt thereof (hereinafter, it will be referred to as "the compound (13)") can be produced by deprotection (elimination of $R^1$) of an $OR^1$ group in the compound (12).

There is no particular limitation for a method of deprotection and examples thereof are a deprotection method using an acid or a base by a known method mentioned in the document [refer to "Protective Groups in Organic Synthesis" by T. W. Greene, John Wiley & Sons (1981)] or a method similar thereto and a deprotection method by means of catalytic reduction.

As to the acid therefor, there are exemplified Brønsted acid such as hydrogen bromide (or hydrobromic acid) and hydrogen iodide (or hydriodic acid); an organic acid such as TFA and acetic acid; and Lewis acid such as $AlCl_3$, aluminum bromide, boron trichloride and boron tribromide.

As to the base, there are exemplified potassium hydroxide and calcium hydroxide.

There is no particular limitation for the amount of the acid or the base used therefor and the amount for 1 mol of the compound (12) is usually 1 to 20 mol and, preferably, 1 to 10 mol.

The deprotection reaction using the acid or the base can be carried out without a solvent or in a solvent. When a solvent is used, there is no particular limitation for the solvent provided that it does not badly affect the reaction and there are exemplified an organic solvent (such as formic acid, acetic acid and propionic acid); an aprotic solvent (such as acetonitrile, DMF and DMSO); a halogenated hydrocarbon solvent (such as DCM and DCE); and a mixed solvent thereof. Among those, preferred ones are a solution of hydrogen bromide in acetic acid and a solution of boron tribromide in DCM and more preferred one is a solution of hydrogen bromide in acetic acid.

In the case of the deprotection method using an acid or a base, there is no particular limitation for the reaction temperature therefor and, usually, the reaction can be carried out under any of cooling, room temperature and heating. Preferably, the reaction is to be carried out for 1 to 24 hour(s) under the temperature condition of from about −78° C. to −70° C.

As to the deprotection method by means of catalytic reduction, there are exemplified a method by hydrogenolysis using a transition metal catalyst such as Pd, Pt, Ru and Rh; and a method by means of hydrogenolysis using a catalyst carrying a transition metal such as Pd—C and palladium hydroxide-carbon (Pearlman's catalyst). Among them, a preferred transition metal catalyst is Pd—C.

Amount of the transition metal catalyst used for 1 mol of the compound (12) is usually 0.01 to 5 mol and, preferably, 0.05 to 0.2 mol.

The reaction by means of catalytic reduction is carried out usually under hydrogen atmosphere of 1 to 4 atmospheric pressure and, preferably, 1 to 2 atmospheric pressure.

The reaction is usually carried out in a solvent. As to the solvent, there is no particular limitation provided that it does not participate in the reaction and examples thereof are an alcohol solvent (such as methanol and ethanol); an ether solvent (such as THF, MTBE, dioxane, diethyl ether, dimethoxyethane and diglyme); an ester solvent (such as methyl acetate and ethyl acetate); a halogenated hydrocarbon solvent (such as DCM and DCE); water; and a mixed solvent thereof. Preferred one is an alcohol solvent (such as methanol and ethanol).

There is no particular limitation for the reaction temperature in the deprotection method by means of catalytic reduction and, usually, the reaction is carried out under any of cooling, room temperature and heating. Preferably, the reaction is to be carried out for 1 to 24 hour(s) under the temperature condition of from room temperature to about 40° C.

When Brønsted acid such as hydrobromic acid is used in the reaction of the step (i), the OR' group in the compound (12) is deprotected an d, at the same time, a salt of the compound represented by the formula (13) is produced.

When a salt of the resulting compound represented by the formula (13) is appropriately neutralized using a base (neutralizing step), a compound represented by the formula (13) (a free base) can be produced.

Usually, the reaction of the neutralizing step can be carried out in a solvent.

As to the solvent, any solvent may be used provided that it does not badly affect the reaction and examples thereof are water; an alcohol solvent (such as methanol, ethanol, isopropanol, n-butanol, trifluoroethanol and ethylene glycol); an ether solvent (such as THF, MTBE, dioxane, diethyl ether, dimethoxyethane and diglyme); an aprotic polar solvent (such as acetonitrile, DMF and DMSO); and a mixed solvent thereof. Preferred one is a mixed solvent of water with an alcohol solvent (particularly, methanol or ethanol). When the solvent used is the same solvent used in the above deprotection step, the reaction of this neutralizing step may be carried out by means of a one-pot synthesis.

As to the base, there may be used known inorganic base and organic base.

As to the inorganic base, there are exemplified aqueous ammonia, alkali metal hydrogen carbonate (such as lithium hydrogen carbonate, sodium hydrogen carbonate and potassium hydrogen carbonate), alkali metal hydroxide (such as lithium hydroxide, sodium hydroxide, potassium hydroxide and cesium hydroxide), alkali metal carbonate (such as lithium carbonate, sodium carbonate, potassium carbonate and cesium carbonate) and alkali metal lower (having 1 to 4 carbon(s) alkoxide (such as sodium methoxide, sodium ethoxide and potassium t-butoxide).

As to the organic base, there are exemplified trialkylamine (such as trimethylamine, triethylamine and N,N-diisopropylethylamine), pyridine, quinoline, piperidine, imidazole, picoline, 4-dimethylaminopyridine, N,N-dimethyl-aniline, N-methylmorpholine, DBN, DABCO and DBU. When the base is liquid, it is also able to be used as a solvent. Each of the bases may be used solely or two or more thereof may be used jointly. Preferred ones are alkali metal carbonate (particularly, sodium carbonate, potassium carbonate and cesium carbonate) and alkali metal lower (having 1 to 4 carbon(s)) alkoxide (such as potassium t-butoxide).

There is no particular limitation for the amount of the base used therefor and, for example, the amount for 1 mol of the compound (12) is usually 0.5 to 10 mol and, preferably, 0.8 to 5 mol.

There is no particular limitation for the reaction temperature of the neutralizing step and, usually, the reaction is carried out under any of cooling, room temperature and heating. Preferably, the reaction is to be carried out for 10 minutes to 30 hours under the temperature condition of from about room temperature to about 100° C.

Each of the aimed compounds produced in each of the above steps (step a to step i) can be isolated and purified from the reaction mixture by such a means that the reaction mixture is cooled for example and the resulting crude reaction product is separated by an isolating operation such as filtration, concentrating and extraction followed by subjected to a common purifying operation such as column chromatography and recrystallization. It is also possible that the resulting one is used for the next reaction without isolation and purification.

2. Process for Producing the Compound (4)

The compound (4) may, for example, be produced via each of the steps shown in the following reaction formula 2. To be more specific, the compound (4) can be produced by way of a step where the compound represented by the formula (1) or a salt thereof (hereinafter, it will be referred to as "the compound (1)") is made to react with hydroxylamine hydrochloride to give a compound represented by the formula (2) or a salt thereof (hereinafter, it will be referred to as "the compound (2)"), a step where the resulting compound (2) is made to react with methanesulfonyl chloride (MsCl) to give a compound represented by the formula (3) or a salt thereof (hereinafter, it will be referred to as "the compound (3)") and a step where the compound (3) is subjected to Beckmann rearrangement in a mixed solvent of DCM with water.

Reaction formula 2

[chem. 13]

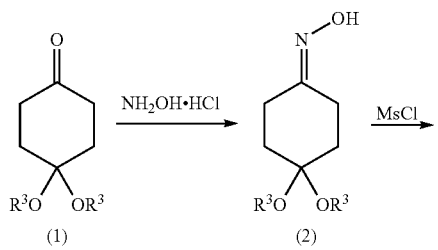

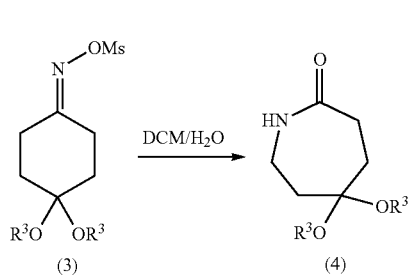

(In the formulae, $R^3$ has the same meanings as mentioned already and Ms stands for a mesyl group.)

EXAMPLES

The present invention will now be specifically illustrated by way of Referential Examples and Examples although the present invention shall not be limited thereto.

Melting point was measured using a melting point measuring device (type MP-21, Yamato) and the thermometer was not corrected.

Nuclear magnetic resonance spectra ($^1$H-NMR) were measured using a nuclear magnetic resonance device (type AVANCE III 500, Bruker BioSpin) where tetramethylsilane (TMS) (δ=0) was used as an internal standard substance.

Mass spectrum (MS) was measured using POLARIS Q (Thermo Fisher Scientific).

Silica gel column chromatography was carried out using silica gel PSQ-1008 (Fuji Silysia Chemical LtD.) or Wako-gel C-300HG (Wako Pure Chemical Industries, LtD.).

In conducting thin-layer chromatography, Silica gel F254 (Merck, No. 5715) or TLC plate NH (Fuji Silysia Chemical LtD.) was used and the detection was done using an UV lamp and a 5 w/v % ethanolic solution of phosphomolybdic acid as a coloring reagent. As to the reagent and the solvent, commercially available ones were used just as they were.

Referential Example 1

The compound (4a) was produced according to the following reaction formula 3.

Reaction formula 3

[chem. 14]

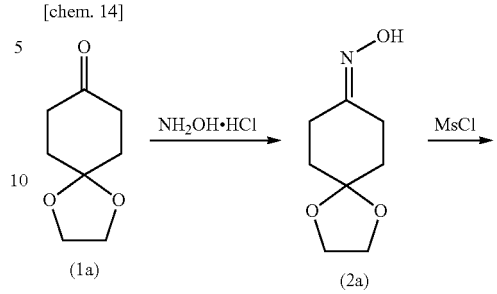

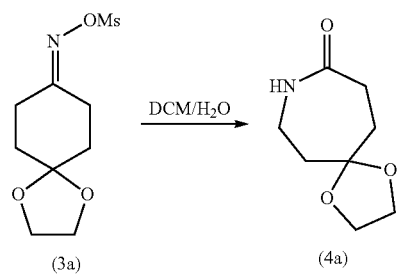

Synthesis of
1,4-dioxa-9-azaspiro[4.6]undecan-8-one (4a)

Under a nitrogen atmosphere, water (5.0 kg) and sodium hydrogen carbonate (592 g, 7.0 ml) were successively added at room temperature to a solution of 1,4-cyclohexandione monoethylene acetal (la) (1.0 kg, 6.4 mol) in DCM (6.7 kg). After that, hydroxylamine hydrochloride (490 g, 7.1 mol) was added thereto by dividing into several times followed by stirring at room temperature for 12 hours. The DCM layer was separated and then water (3.74 kg) and sodium hydrogen carbonate (1.62 kg, 19.3 mol) were successively added thereto at room temperature. After MsCl (998 g, 7.0 mol) was gradually dropped into the reaction mixture at 0° C. to 5° C., temperature of the mixture was raised to room temperature followed by stirring for 2 days. The DCM layer was separated and an aqueous layer was extracted with DCM (4×4.98 kg). The DCM layers were combined, the solvent was distilled off therefrom at 35° C. to 42° C., toluene (2.6 kg) was added to the residue followed by stirring for 1 hour at 55° C. to 60° C. Heptane (4.2 kg) was further added thereto followed by stirring for 1 hour at 55° C. to 60° C. The solid deposited therefrom was collected by filtration and dried in vacuo at 35° C. to 45° C. to give 795 g (73%) of the title compound (4a).

Compound (4a):

Melting point: 93° C. to 95° C.

$^1$H-NMR (CDCl$_3$) δ: 1.78-1.88 (m, 4H), 2.48-2.55 (m, 2H), 3.24-3.32 (m, 2H), 3.94-4.02 (m, 4H), 6.06 (s, 1H).

Example 1

The compound (13a) was produced according to the following reaction formula 4.

Reaction formula 4
[chem. 15]
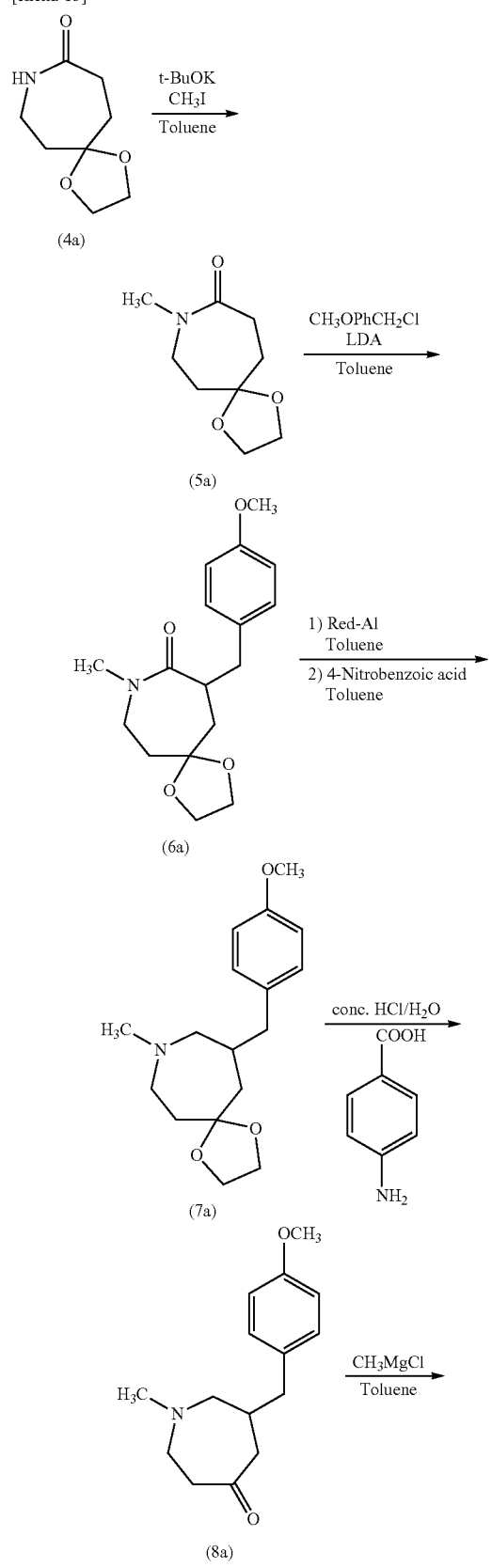
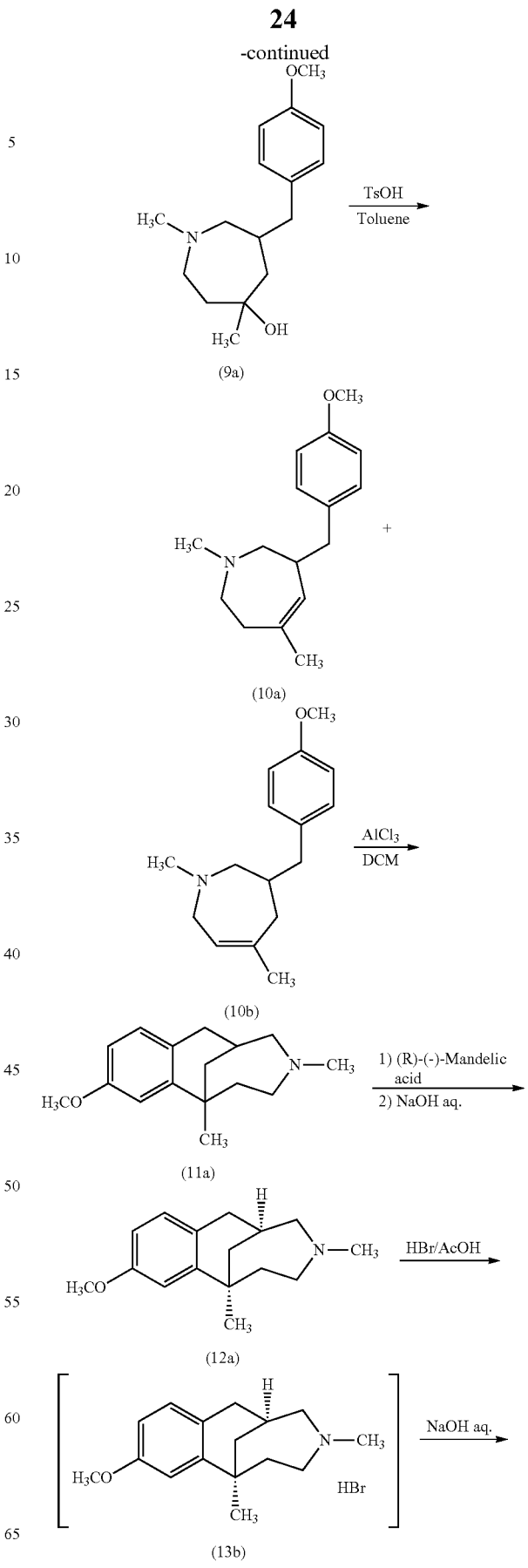

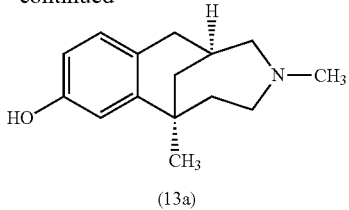

(13a)

(1-1) Synthesis of 9-methyl-1,4-dioxa-9-azaspiro-[4.6]undecan-8-one (5a): Step (a)

Under nitrogen atmosphere, a mixture of the compound (4a) (774 g, 4.5 mol) and toluene (6.7 kg) was stirred at room temperature for 30 minutes and potassium t-butoxide (760 g, 6.8 mol) was gradually added thereto. After the mixture was stirred at room temperature for 1 hour, methyl iodide (950 g, 6.7 mol) was gradually dropped thereinto followed by stirring for 1 hour more. The reaction was stopped by addition of water (800 g) thereto and, after that, a toluene layer was separated out therefrom and then an aqueous layer was extracted with dichloromethane (2×2.8 kg). An organic layer was concentrated in vacuo at 35° C. to 45° C. to give 814.5 g (97%) of the title compound 5a as an amorphous solid.

Compound (5a):
$^1$H-NMR (CDCl$_3$) δ: 1.75-1.86 (m, 4H), 2.52-2.60 (m, 2H), 3.00 (s, 3H), 3.36-3.46 (m, 2H), 3.92-4.01 (m, 4H)

(1-2) Synthesis of 10-[(4-methoxyphenyl)methyl]-8-methyl-1,4-dioxa-8-azaspiro[4.6]undecan-9-one (6a): Step (b)

Under nitrogen atmosphere, a 2.5 mL/L solution of n-butyl lithium in hexane (2.1 L, 5.3 mol) was gradually dropped into a solution of diisopropylamine (540 g, 5.3 mol) in toluene (3.5 kg) at −20° C. to 10° C. followed by stirring for 3 hours. After that, a solution of the compound 5a (800 g, 4.3 mol) in toluene (3.5 kg) was gradually dropped thereinto at −5° C. to 0° C., the mixture was stirred for 1 hour and then 4-methoxybenzyl chloride (680 g, 4.3 mol) was gradually dropped thereinto at −5° C. to 0° C. After the mixture was stirred at −5° C. to 5° C. for 1 hour, 0.5 mol/1 hydrochloric acid (14.0 kg, corresponding to 7 mol as hydrogen chloride) was gradually dropped thereinto at 0° C. to 10° C. followed by stirring for 30 minutes. The organic layer was separated therefrom, washed with 10 wt % aqueous solution of sodium hydrogen carbonate (2.0 g) and concentrated in vacuo at 30° C. to 40° C. to give 945 g (72%) of the title compound as an oily substance.

Compound (6):
$^1$H-NMR (CDCl$_3$) δ: 1.52 (dd, J=11.1, 14.1 Hz, 1H), 1.72-1.77 (m, 3H), 2.53 (dd, J=9.4, 14.4 Hz, 1H), 2.93-3.00 (m, 1H), 3.02 (s, 3H), 3.03-3.10 (m, 1H), 3.18 (dd, J=5.5, 14.4 Hz, 1H), 3.45-3.49 (m, 1H), 3.76-3.88 (m, 7H), 6.81-6.86 (m, 2H), 7.16 (d, J=8.7 Hz, 2H).

(1-3) Synthesis of 10-[(4-methoxyphenyl)methyl]-8-methyl-1,4-dioxa-8-azaspiro[4.6]undecane 4-nitrobenzoate (7a): Step (c)

Under nitrogen atmosphere, a solution of the compound 6a (900 g, 2.9 mol) in toluene (4.5 kg) was gradually dropped into a 70 wt % solution of Red-Al in toluene (3.4 kg, 11.8 mol as Red-Al) at 15° C. to 25° C. followed by stirring at 15° C. to 25° C. for 2 hours. Under cooling with ice, a 30 wt % aqueous solution of potassium sodium tartrate (6.7 kg) was carefully added thereto, the mixture was stirred for 30 minutes and a toluene layer was separated therefrom. 4-Nitrobenzoic acid (0.46 kg, 2.8 mol) was added to the toluene layer at 15° C. to 25° C. followed by stirring for 2 hours. The solid deposited therefrom was collected by filtration to give 1.16 kg (86%) of the title compound 7a.

Compound (7a):
Melting point: 97-100° C.
$^1$H-NMR (DMSO-d$_6$) δ: 1.66 (dd, J=10.5, 14.3 Hz, 1H), 1.72-1.76 (m, 1H), 1.88-1.94 (m, 2H), 2.08-2.25 (m, 1H), 2.36-2.53 (m, 6H), 2.66-2.78 (m, 1H), 2.81-2.92 (m, 2H), 3.58-3.63 (m, 1H), 3.70-3.83 (m, 6H), 6.84 (d, J=8.5 Hz, 2H), 7.09 (d, J=8.5 Hz, 2H), 8.11 (d, J=8.7 Hz, 2H), 8.25 (d, J=8.7 Hz, 2H).

(1-4) Synthesis of 6-[(4-methoxyphenyl)methyl]-1-methylazepan-4-one (8a): Step (d)

Under nitrogen atmosphere, a mixture of the compound 7a (1.16 kg, 2.5 mol) and 6 mol/L hydrochloric acid (4.4 kg, 28.8 mol as hydrogen chloride) was stirred at 25° C. for 2 hours and, after that, the solid was filtered off. The filtrate was adjusted to pH 10 to 12 using a 50 wt % aqueous solution of sodium hydroxide and extracted with toluene (5.5 kg). The organic layer was concentrated in vacuo at 45° C. to 55° C. to give 575 g (92%) of the title compound 8a as an oily product.

Compound (8):
$^1$H-NMR (CDCl$_3$) δ: 2.18-2.31 (m, 2H), 2.34 (s, 3H), 2.36-2.42 (m, 1H), 2.45-2.53 (m, 3H), 2.54-2.63 (m, 2H), 2.73-2.84 (m, 3H), 3.78 (s, 3H), 6.83 (d, J=8.5 Hz, 2H), 7.05 (d, J=8.5 Hz, 2H).

(1-5) Synthesis of 6-[(4-methoxyphenyl)methyl]-1,4-dimethylazepan-4-ol (9a): Step (e)

Under nitrogen atmosphere, a solution of the compound 8a (378 g, 1.5 mol) in toluene (1.1 kg) was gradually dropped into a 3.0 mol/L solution of methyl magnesium chloride in THF (2 L, 6.0 mol as methyl magnesium chloride) at 0° C. to 5° C. followed by stirring for 30 minutes. After the reaction mixture was carefully added to ice water (3 kg) at 0° C. to 20° C., a toluene layer was separated and an aqueous layer was extracted with toluene (3.8 kg). The organic layers were combined and concentrated in vacuo at 45° C. to 55° C. to give 378 g (88%) of the title compound 9a as an oily product.

Compound (9a):
$^1$H-NMR (CDCl$_3$) δ: 1.13-1.22 (m, 3H), 1.60-2.02 (m, 4H), 2.13-2.88 (m, 10H), 3.79 (s, 3H), 6.79-6.84 (m, 2H), 7.02-7.08 (m, 2H).

(1-6) Synthesis of 3-[(4-methoxyphenyl)methyl]-1,5-dimethyl-2,3,6,7-tetrahydroazepine (10a) and 3-[(4-methoxy-phenyl)methyl]-1,5-dimethyl-2,3,4,7-tetrahydroazepine (10b): Step (f)

p-TsOH (1.0 g, 5.7 mmol) was added to a solution of the compound 9a (0.5 g, 1.9 mmol) in toluene (5 mL) and the mixture was heated to reflux for 20 hours. After the reaction mixture was allowed to cool, it was adjusted to pH 12~13 using a 10 wt % aqueous solution of sodium hydroxide and extracted with ethyl acetate (10 mL). After the ethyl acetate layer was dried over anhydrous sodium sulfate, the solvent was evaporated to dryness in vacuo and the resulting residue was isolated/purified by silica gel column chromatography (Wakogel C-300HG, chloroform:methanol=99:1) to give the title compounds 10a (0.02 g, 4%) and 10b (0.01 g, 2%) as an oil product each.

Compound (10a):

$^1$H-NMR (CDCl$_3$) δ: 1.70 (s, 3H), 2.10 (dd, J=7.5, 15.8 Hz, 1H), 2.15 (dd, J=1.9, 11.9 Hz, 1H), 2.22-2.28 (m, 1H), 2.33 (s, 3H), 2.44 (dd, J=10.1, 15.7 Hz, 1H), 2.52-2.63 (m, 2H), 2.70-2.77 (m, 1H), 2.68 (d, J=12.1, 1H), 2.80 (dd, J=7.5, 11.7 Hz, 1H), 3.78 (s, 3H), 5.31-5.35 (m, 1H), 6.82 (d, J=8.5 Hz, 2H), 7.11 (d, J=8.4 Hz, 2H).

MS (EI): m/z 245 [M]$^+$.

Compound (10b):

$^1$H-NMR (CDCl$_3$) δ: 1.67 (s, 3H), 1.99 (d, J=15.1 Hz, 1H), 2.00-2.09 (m, 1H), 2.18 (dd, J=10.0, 15.0 Hz, 1H), 2.29 (s, 3H), 2.40 (d, J=12.1 Hz, 1H), 2.43 (dd, J=7.1, 13.8 Hz, 1H), 2.51 (dd, J=7.1, 13.8 Hz, 1H), 2.71 (dd, J=3.8, 12.1 Hz, 1H), 2.92-3.04 (m, 2H), 3.79 (s, 3H), 5.45-5.50 (m, 1H), 6.82 (d, J=8.6 Hz, 2H), 7.07 (d, J=8.6 Hz, 2H).

MS (EI): m/z 245 [M$^+$].

(1-7) Synthesis of the Compound (10a) and the Compound (10b): Step (f)

The same process as in the above (1-6) was carried out except that p-TsOH was changed to P$_2$O$_3$ to produce the compound 10 (84.1%).

(1-8) Synthesis of the Compound (10a) and the Compound (10b): Step (f)

The same process as in the above (1-6) was carried out except that p-TsOH was changed to BF$_3$.Et$_2$O complex to produce the compound 10 (93.8%).

(1-9) Synthesis of the Compound (10a) and the Compound (10b): Step (f)

The same process as in the above (1-6) was carried out except that p-TsOH was changed to TFA/TFAA to produce the compound 10 (80.4%).

(1-10) Synthesis of the Compound (10a) and the Compound (10b): Step (f)

The same process as in the above (1-6) was carried out except that p-TsOH was changed to MsOH to produce the compound 10 (71%).

(1-11) Synthesis of the Compound (10a) and the Compound (10b): Step (f)

The same process as in the above (1-6) was carried out except that p-TsOH was changed to TfOH to produce the compound 10 (87%).

The yields shown in the above (1-7) to (1-11) are the reaction yields by taking out the crude reaction solution followed by determining by means of high-performance liquid chromatography.

(1-12) Synthesis of 2,3,4,5,6,7-hexahydro-1,4-dimethyl-10-methoxy-1,6-methano-1H-4-benzoazonine (11a): Step (g)

A mixture (1.18 g, 4.8 mmol) of the compound l0a and the compound 10b dissolved in anhydrous DCM (5 mL) was dropped into a mixture of aluminum chloride (1.9 g, 14.2 mmol) and anhydrous DCM (5 mL) during 3 minutes under cooling with ice. After stirring at room temperature for 5 hours, the reaction mixture was added to water (5 mL) at the temperature of not higher than 10° C. After adjusting the pH to 10~11 using a 15 wt % aqueous solution of sodium hydroxide, ethyl acetate (100 mL) was added thereto and the solid was removed using Celite. An organic layer was separated therefrom and an aqueous solution was extracted with ethyl acetate (50 mL). The organic layers were combined and dried over anhydrous sodium sulfate. After that, the solvent was evaporated in vacuo and the resulting residue was purified by means of silica gel column chromatography (PSQ-100B, chloroform:methanol=49:1) to give the title compound 11a (1.15 g, 97%) as an oily product.

Compound (11a):

$^1$H-NMR (CDCl$_3$) δ: 1.26 (s, 3H), 1.65-1.78 (m, 4H), 1.81 (dd, J=7.1, 13.4 Hz, 1H), 2.18-2.26 (m, 4H), 2.34-2.41 (m, 1H), 2.42-2.49 (m, 1H), 2.56-2.62 (m, 1H), 2.80 (dd, J=4.5, 15.5 Hz, 1H), 2.98-3.06 (m, 1H), 3.79 (s, 3H), 6.69 (dd, J=2.7, 8.4 Hz, 1H), 6.79 (d, J=2.7 Hz, 1H), 6.99 (d, J=8.3 Hz, 1H).

MS (E/I): m/z 245 [M]$^+$.

Example 2

(2-1) Synthesis of 2,3,4,5,6,7-hexahydro-1,4-dimethyl-10-methoxy-1,6-methano-1H-4-benzoazonine (11a): One-Pot Synthesis: Steps (f) and (g)

Under nitrogen atmosphere, p-TsOH (196 g, 1.1 mol) was added to a solution of the compound 9a (100 g, 0.38 mol) in toluene (600 g) at 25° C. followed by heating to reflux for 20 hours. After being allowed to cool, water (800 g) was gradually dropped thereinto at 15° C. to 25° C. followed by stirring for 30 minutes. An aqueous layer was separated, adjusted to pH 12~13 at 15° C. to 25° C. using a 30 wt % aqueous solution of sodium hydroxide and extracted with MTBE (2×1 L). After an organic layer was concentrated in vacuo at 25° C. to 35° C., the residue was diluted with dichloromethane (500 mL). This diluted solution was gradually dropped, at 0° C. to 5° C., into a mixture of aluminum chloride (151 g, 1.13 mol) and DCM (500 mL) followed by stirring for 30 minutes. After that, temperature of the above was raised to 15° C.~25° C. followed by stirring for 20 hours. The reaction mixture was dropped into water (1 L) at 0° C. to 10° C. followed by adjusting the pH to 12~13 at 15° C. to 25° C. using a 30 wt % aqueous solution of sodium hydroxide. This was extracted with MTBE (2×1 L) and organic layers were combined followed by concentrating in vacuo at 15° C. to 25° C. to give 68 g (73%) of the title compound 11a as an oily product.

Example 3

(3-1) Synthesis of (−)-(1S,6S)-2,3,4,5,6,7-hexahydro-1,4-dimethyl-10-methoxy-1,6-methano-1H-4-benzoazonine (12a): Step (h)

D-Mandelic acid (9.5 g, 0.06 mol) was added to a solution of the compound 11a (31.6 g, 0.13 mol) in MTBE (310 mL) at 15° C. to 25° C. followed by stirring for 1 hour. The deposited solid was collected by filtration and washed with MTBE (31 mL). A 1 mol/L aqueous solution of sodium hydroxide (49 mL, 49 mmol as sodium hydroxide) was added to the resulting solid at 15° C. to 25° C. followed by stirring for 1 hour. This was extracted with toluene (2×150 mL) and concentrated in vacuo at 45° C. to 55° C. to give 12.0 g (38%) of the title compound 12a as an oily product.

Compound (12a):

$^1$H-NMR (CDCl$_3$) δ: 1.26 (s, 3H), 1.65-1.78 (m, 4H), 1.81 (dd, J=7.1, 13.4 Hz, 1H), 2.18-2.26 (m, 4H), 2.34-2.41 (m, 1H), 2.42-2.49 (m, 1H), 2.56-2.62 (m, 1H), 2.80 (dd, J=4.5, 15.5 Hz, 1H), 2.98-3.06 (m, 1H), 3.79 (s, 3H), 6.69 (dd, J=2.7, 8.4 Hz, 1H), 6.79 (d, J=2.7 Hz, 1H), 6.99 (d, J=8.3 Hz, 1H).

MS (EI): m/z 245 [M]+

(3-2) Synthesis of (−)-(1S,6S)-2,3,4,5,6,7-hexahydro-1,4-dimethyl-1,6-methano-1H-4-benzoazonin-10-ol (Eptazocine): Step (i)

Under nitrogen atmosphere, the compound 12a (10 g, 0.04 mol) was added to a 48 wt % solution of hydrogen bromide in acetic acid (50 mL) at 10° C. to 20° C. followed by stirring for 15 minutes. This was warmed at 35° C. to 40° C. and stirred for 12 hours. After the reaction mixture was allowed to stand, it was concentrated in vacuo. Further, toluene (100 mL) was added to the residue and acetic acid was azeotropically distilled whereupon a solid 13b was prepared. The resulting solid was dissolved in water (200 mL) and its pH was adjusted to 11-12 using a 2.5 mol/L aqueous solution of sodium hydroxide. After it was stirred at 20° C. to 30° C. for 8 hours under nitrogen atmosphere, its pH was adjusted to 7-8 by 6 mol/L hydrochloric acid and the suspension was stirred for 1 hour. The solid was collected by filtration and washed with water (50 mL). After that, the solid was added to ethanol (300 mL) and the resulting slurry was stirred for 1 hour at 70° C. to 75° C. and allowed to cool down to 20° C.~30°. The solid was collected by filtration, washed with ethanol (50 mL) and dried at 70° C. to 80° C. in vacuo to give 8.2 g (87%) of the title compound 13a.

Compound (13a):
$^1$H-NMR (DMSO-$d_6$) δ: 1.16 (s, 3H), 1.50-1.65 (m, 4H), 1.66-1.71 (m, 1H), 2.08-2.16 (m, 4H), 2.23-2.35 (m, 2H), 2.48-2.53 (m, 1H), 2.68 (dd, J=4.5, 15.3 Hz, 1H), 2.87-2.93 (m, 1H), 6.50 (dd, J=2.5, 8.1 Hz, 1H), 6.63 (d, J=2.5 Hz, 1H).

The invention claimed is:

1. A tetrahydroazepine compound represented by the formula (10) or a salt thereof,

[chem. 1]

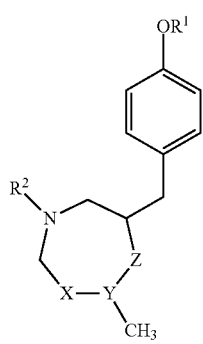

(10)

wherein in the formulae,
R$^1$ is an alkyl group optionally substituted with halogen atom, aryl group, alkoxy group, allyl group or vinyl group,
R$^2$ is an alkyl group optionally substituted with halogen atom, aryl group, alkoxy group, allyl group or vinyl group and
one of the X—Y bond and the Y—Z bond is a carbon-carbon double bond and the other is a carbon-carbon single bond.

2. The compound or the salt thereof according to claim 1, wherein R$^1$ is methyl group and R$^2$ is methyl group in the formula (10).

3. A process for producing the tetrahydroazepine compound or the salt thereof according to claim 1, comprising
(f): a step where a compound represented by the formula (9) or a salt thereof is made to react with at least one dehydrating agent selected from the group consisting of boron trifluoride ether complex, trifluoroacetic acid, trifluoroacetic acid anhydride, trimethylsilyl trifluoromethanesulfonate, aluminum chloride, titanium (IV) chloride, tin (IV) chloride, triphenylmethyl perchlorate, bismuth triflate, ytterbium triflate, scandium triflate, trifluoromethanesulfonic acid, methanesulfonic acid, p-toluenesulfonic acid, benzenesulfonic acid, 10-camphorsulfonic acid and phosphorus pentaoxide,

[chem. 2]

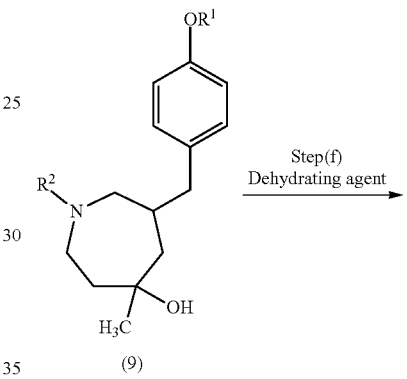

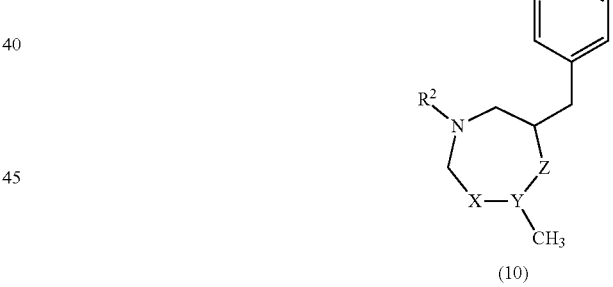

wherein in the formulae,
R$^1$ is an alkyl group optionally substituted with halogen atom, aryl group, alkoxy group, allyl group or vinyl group,
R$^2$ is an alkyl group optionally substituted with halogen atom, aryl group, alkoxy group, allyl group or vinyl group and
one of the X—Y bond and the Y—Z bond is a carbon-carbon double bond and the other is a carbon-carbon single bond.

4. The process according to claim 3, further comprising
(e): a step where a compound represented by the formula (8) or a salt thereof is made to react with a methylating agent to give a compound represented by the formula (9) or a salt thereof,

[chem. 3]

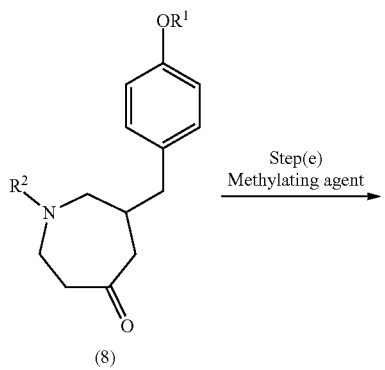

wherein in the formulae,

R[1] is an alkyl group optionally substituted with halogen atom, aryl group, alkoxy group, allyl group or vinyl group, R[2] is an alkyl group optionally substituted with halogen atom, aryl group, alkoxy group, allyl group or vinyl group and the two R[3]'s are the same or different, and each is an alkyl group optionally substituted with halogen atom, aryl group, alkoxy group, allyl group or vinyl group, or the two R[3]'s may be bonded to each other to form a ring together with oxygen atoms to which the two R[3]'s are bonded.

6. The process according to claim 5, further comprising (c): a step where a compound represented by the formula (6) or a salt thereof is made to react with a reducing agent to give a compound represented by the formula (7) or a salt thereof,

[chem. 5]

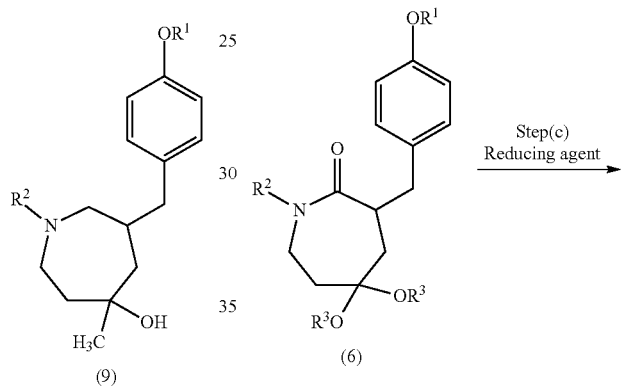

wherein in the formulae, R[1] and R[2] have the same meanings as mentioned in claim 3.

5. The process according to claim 4, further comprising (d): a step where a compound represented by the formula (7) or a salt thereof is made to react with an acid to give a compound represented by the formula (8) or a salt thereof,

[chem. 4]

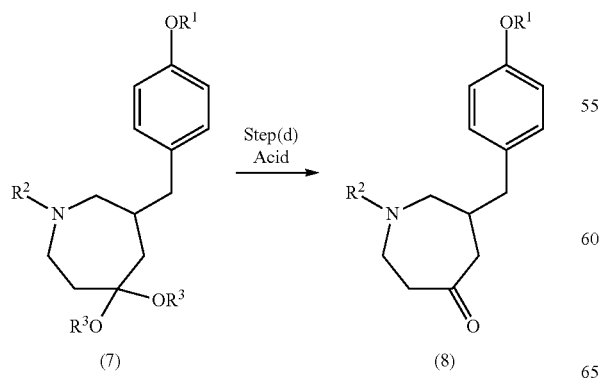

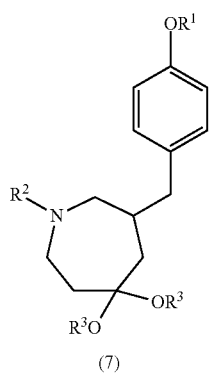

wherein in the formulae,

R[1], R[2] and R[3] have the same meanings as mentioned in claim 5.

7. The process according to claim 6, further comprising (b): a step where a compound represented by the formula (5) or a salt thereof is made to react with a compound represented by the formula (15) to give a compound represented by the formula (6) or a salt thereof,

[chem. 6]

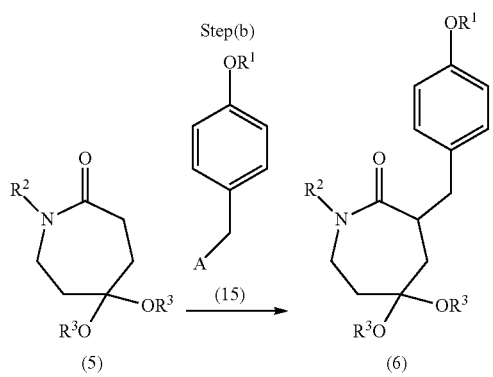

wherein in the formulae, $R^1$ is an alkyl group optionally substituted with halogen atom, aryl group, alkoxy group, allyl group or vinyl group, $R^2$ is an alkyl group optionally substituted with halogen atom, aryl group, alkoxy group, allyl group or vinyl group, the two $R^3$'s are the same or different, and each is an alkyl group optionally substituted with halogen atom, aryl group, alkoxy group, allyl group or vinyl group, or the two $R^3$'s may be bonded to each other to form a ring together with oxygen atoms to which the two $R^3$'s are bonded and A is an eliminating group.

8. The process according to claim 7, further comprising (a): a step where a compound represented by the formula (4) or a salt thereof is made to react with an alkylating agent to give a compound represented by the formula (5) or a salt thereof,

[chem. 7]

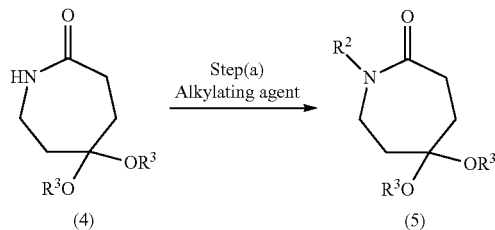

wherein in the formulae, $R^2$ and $R^3$ have the same meanings as mentioned in claim 7.

9. A process for producing the 4-benzoazonine compound represented by the formula (11) or a salt thereof, comprising (g): a step where a tetrahydroazepine compound represented by the formula (10) or a salt thereof is made to react with an acid,

[chem. 8]

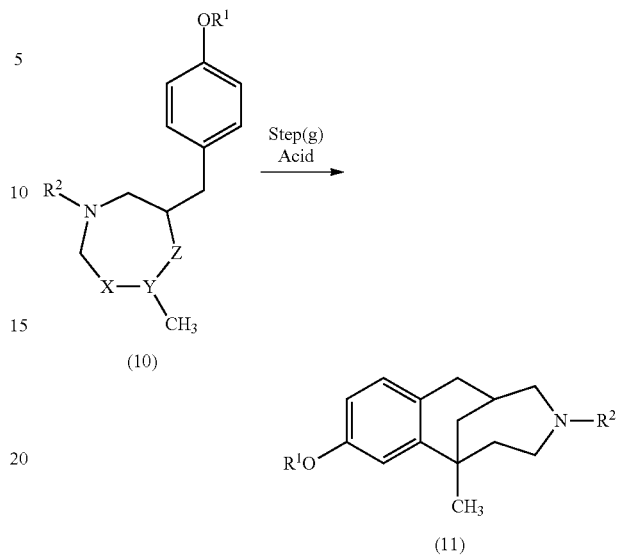

wherein in the formulae, $R^1$ is an alkyl group optionally substituted with halogen atom, aryl group, alkoxy group, allyl group or vinyl group, $R^2$ is an alkyl group optionally substituted with halogen atom, aryl group, alkoxy group, allyl group or vinyl group and one of the X—Y bond and the Y—Z bond is a carbon-carbon double bond and the other is a carbon-carbon single bond.

10. The process according to claim 9, comprising at least one step(s) selected from the group consisting of (a) to (f):

(a): a step where a compound represented by the formula (4) or a salt thereof is made to react with an alkylating agent to give a compound represented by the formula (5) or a salt thereof,

[chem. 9]

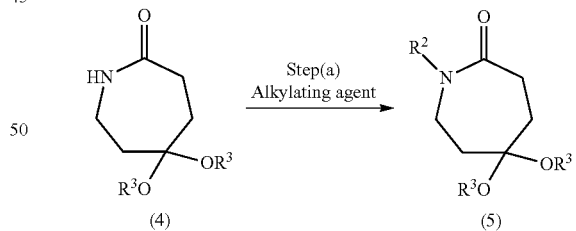

wherein in the formulae, $R^2$ has the same meaning as mentioned in claim 9, and the two $R^3$'s are the same or different, and each is an alkyl group optionally substituted with halogen atom, aryl group, alkoxy group, allyl group or vinyl group, or the two $R^3$'s may be bonded to each other to form a ring together with oxygen atoms to which the two $R^3$'s are bonded;

(b): a step where a compound represented by the formula (5) or a salt thereof is made to react with a compound represented by the formula (15) to give a compound represented by the formula (6) or a salt thereof,

[chem. 10]

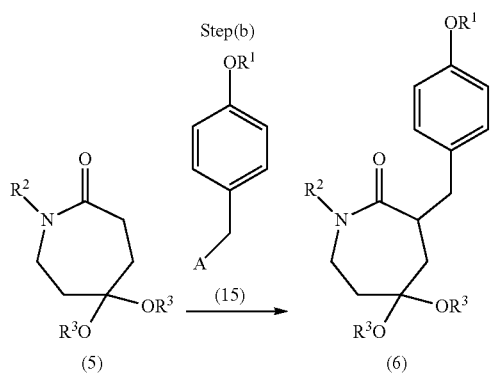

wherein in the formulae, $R^1$ and $R^2$ have the same meanings as mentioned in claim 9, $R^3$ has the same meaning as mentioned in the step (a) and A is an eliminating group;

(c): a step where a compound represented by the formula (6) or a salt thereof is made to react with a reducing agent to give a compound represented by the formula (7) or a salt thereof,

[chem. 11]

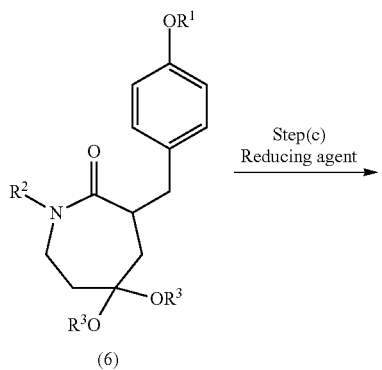

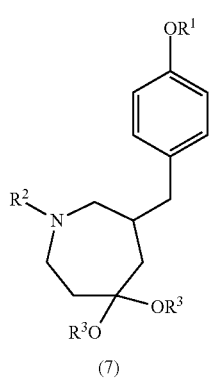

wherein in the formulae, $R^1$ and $R^2$ have the same meanings as mentioned in claim 9, $R^3$ has the same meaning as mentioned in the step (a);

(d): a step where a compound represented by the formula (7) or a salt thereof is made to react with an acid to give a compound represented by the formula (8) or a salt thereof,

[chem. 12]

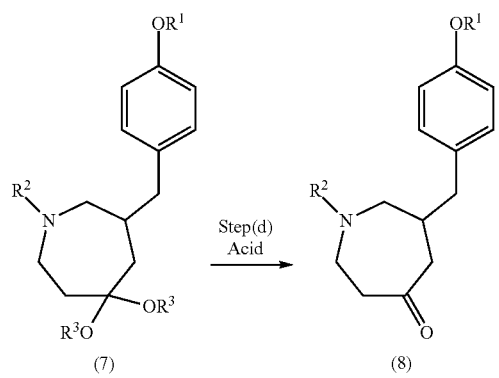

wherein in the formulae, $R^1$ and $R^2$ have the same meanings as mentioned in claim 9, $R^3$ has the same meaning as mentioned in the step (a);

(e): a step where a compound represented by the formula (8) or a salt thereof is made to react with a methylating agent to give a compound represented by the formula (9) or a salt thereof,

[chem. 13]

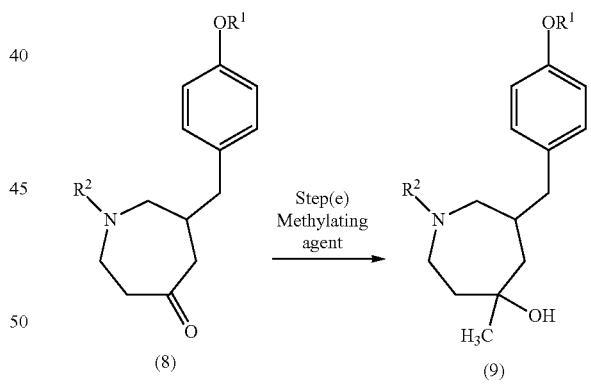

wherein in the formulae, $R^1$ and $R^2$ have the same meanings as mentioned in claim 9; and (f): a step where a compound represented by the formula (9) or a salt thereof is made to react with at least one dehydrating agent selected from the group consisting of boron trifluoride ether complex, trifluoroacetic acid, trifluoroacetic acid anhydride, trimethylsilyl trifluoromethanesulfonate, aluminum chloride, titanium (IV) chloride, tin (IV) chloride, triphenylmethyl perchlorate, bismuth triflate, ytterbium triflate, scandium triflate, trifluoromethanesulfonic acid, methanesulfonic acid, p-toluenesulfonic acid, benzenesulfonic acid, 10-camphorsulfonic acid and phosphorus pentaoxide,

[chem. 14]

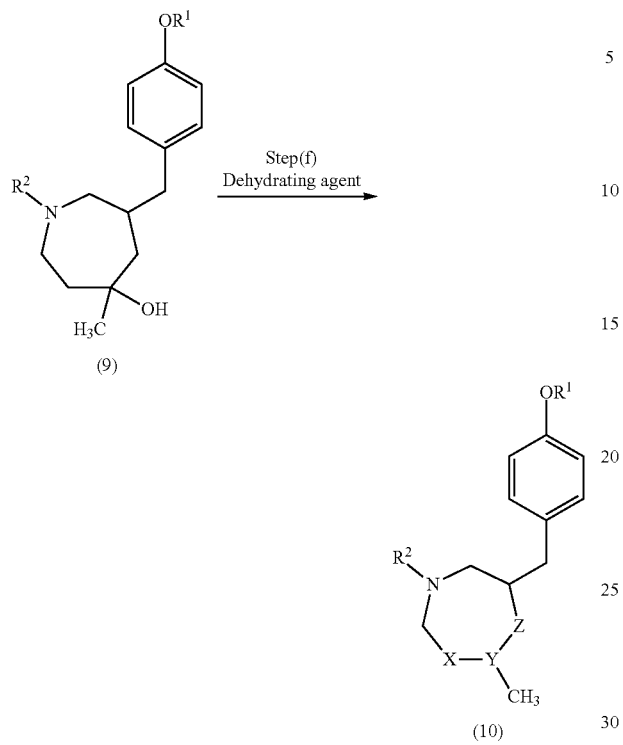

wherein in the formulae, R¹, R², the X—Y bond and the Y—Z bond have the same meanings as mentioned in claim 9.

11. A process for producing a compound represented by the formula (13) or a salt thereof, comprising:
(a): a step where a compound represented by the formula (4) or a salt thereof is made to react with an alkylating agent to give a compound represented by the formula (5) or a salt thereof,

[chem. 15]

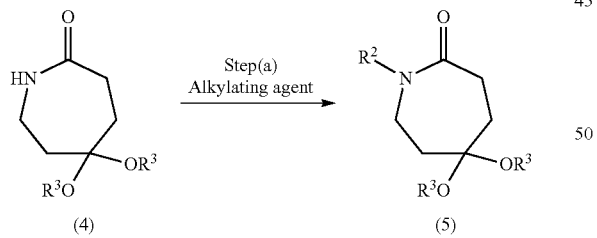

wherein in the formulae,
R² is an alkyl group optionally substituted with halogen atom, aryl group, alkoxy group, allyl group or vinyl group and
the two R³'s are the same or different, and each is an alkyl group optionally substituted with halogen atom, aryl group, alkoxy group, allyl group or vinyl group, or the two R³'s may be bonded to each other to form a ring together with oxygen atoms to which the two R³'s are bonded;
(b): a step where a compound represented by the formula (5) or a salt thereof is made to react with a compound represented by the formula (15) to give a compound represented by the formula (6) or a salt thereof,

[chem, 16]

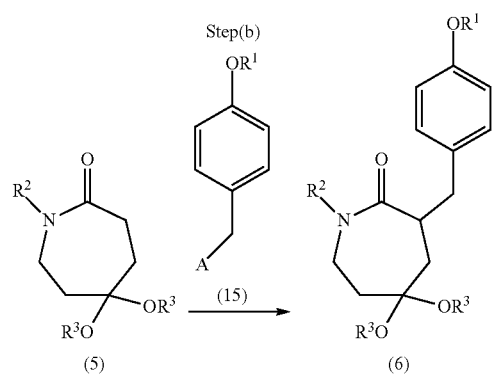

wherein in the formulae, R¹ is an alkyl group optionally substituted with halogen atom, aryl group, alkoxy group, allyl group or vinyl group, R² and R³ have the same meanings as mentioned in the step (a) and A is an eliminating group;
(c): a step where a compound represented by the formula (6) or a salt thereof is made to react with a reducing agent to give a compound represented by the formula (7) or a salt thereof,

[chem. 17]

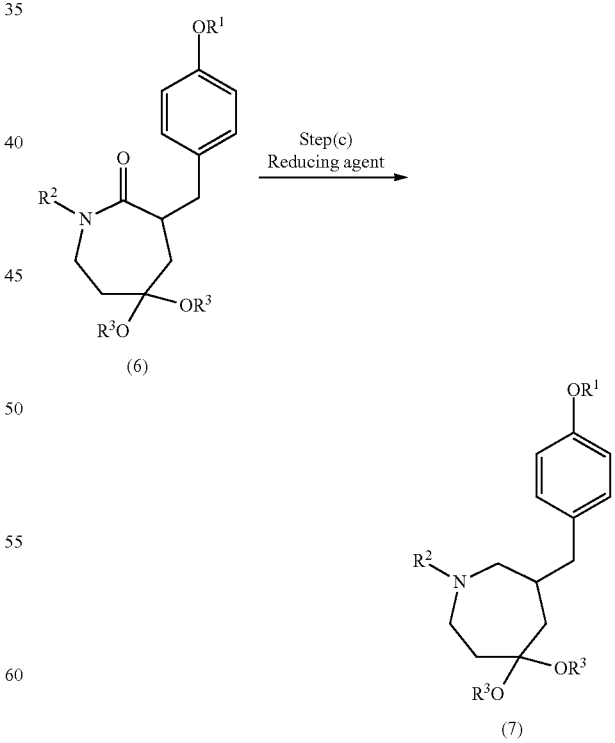

wherein in the formulae, R¹ has the same meaning as mentioned in the step (b), R² and R³ have the same meanings as mentioned in the step (a);

(d): a step where a compound represented by the formula (7) or a salt thereof is made to react with an acid to give a compound represented by the formula (8) or a salt thereof,

[chem. 18]

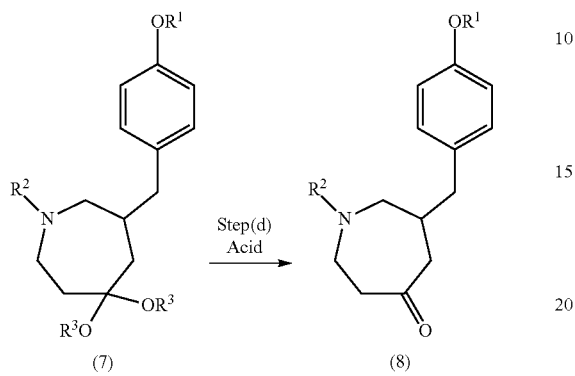

wherein in the formulae, R¹ has the same meaning as mentioned in the step (b), and R² and R³ have the same meanings as mentioned in the step (a);

(e): a step where a compound represented by the formula (8) or a salt thereof is made to react with a methylating agent to give a compound represented by the formula (9) or a salt thereof,

[chem. 19]

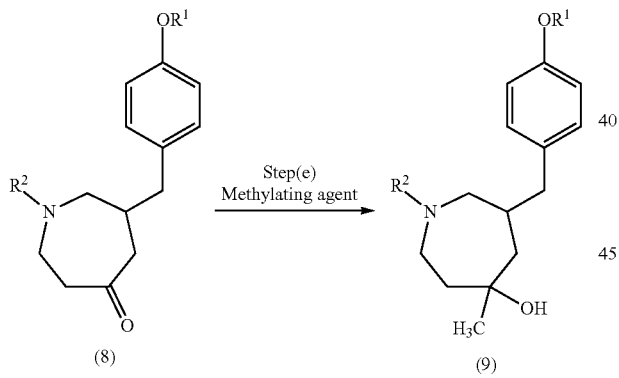

wherein in the formulae, R¹ has the same meaning as mentioned in the step (b), and R² has the same meaning as mentioned in the step (a);

(f): a step where a compound represented by the formula (9) or a salt thereof is made to react with at least one dehydrating agent selected from the group consisting of boron trifluoride ether complex, trifluoroacetic acid, trifluoroacetic acid anhydride, trimethylsilyl trifluoromethanesulfonate, aluminum chloride, titanium (IV) chloride, tin (IV) chloride, triphenylmethyl perchlorate, bismuth triflate, ytterbium triflate, scandium triflate, trifluoromethanesulfonic acid, methanesulfonic acid, p-toluenesulfonic acid, benzenesulfonic acid, 10-camphorsulfonic acid and phosphorus pentaoxide,

[chem. 20]

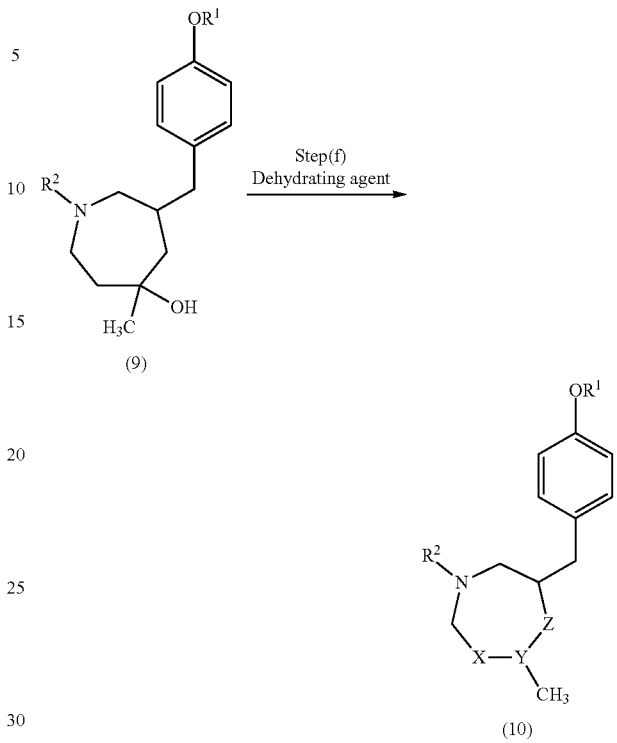

wherein in the formulae, R¹ has the same meaning as mentioned in the step (b), and R² has the same meaning as mentioned in the step (a) and one of the X—Y bond and the Y—Z bond is a carbon-carbon double bond and the other is a carbon-carbon single bond (g): a step where a tetrahydroazepine compound represented by the formula (10) or a salt thereof is made to react with an acid,

[chem. 21]

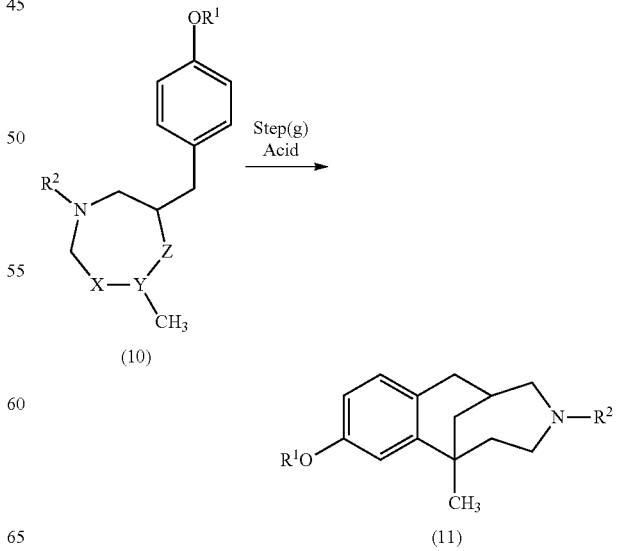

wherein in the formulae, $R^1$ has the same meaning as mentioned in the step (b), and $R^2$ has the same meaning as mentioned in the step (a) and the X—Y bond and the Y—Z bond have the same meanings as mentioned in step (f), (h): a step where a 4-benzoazonine compound represented by the formula (11) or a salt thereof is made to react with an organic acid to give a compound represented by the formula (12) or salt thereof and (i) a step where an $OR^1$ group in the compound represented by the formula (12) or a salt thereof is deprotected to give the compound represented by the formula (13) or a salt thereof,

[chem. 22]

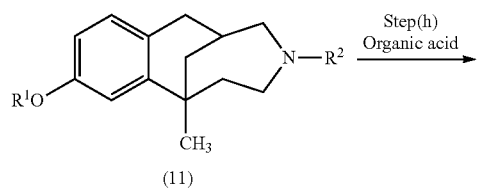

(11)

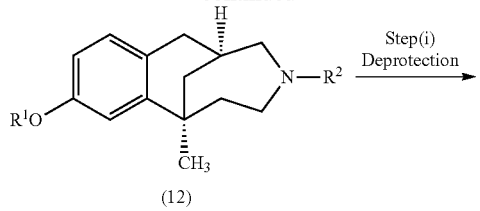

(12)

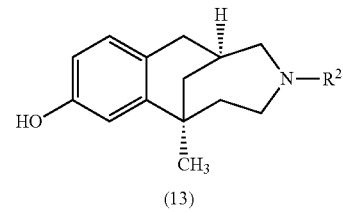

(13)

wherein in the formulae, $R^1$ has the same meaning as mentioned in the step (b), and $R^2$ has the same meaning as mentioned in the step (a).

* * * * *